United States Patent
Luhrs et al.

(10) Patent No.: US 12,280,255 B2
(45) Date of Patent: *Apr. 22, 2025

(54) SURGICAL TOOLS AND METHODS FOR DELIVERING A NEUROSTIMULATOR INTO THE PTERYGOPALATINE FOSSA

(71) Applicant: Realeve, LLC, Manalapan, FL (US)

(72) Inventors: Tom Luhrs, Redwood City, CA (US); Alan Cheng, Redwood City, CA (US); Ryan Powell, Sunnyvale, CA (US); Jennifer Teng, San Francisco, CA (US)

(73) Assignee: REALEVE, LLC, Manalapan, FL (US)

( * ) Notice: Subject to any disclaimer, the term of this patent is extended or adjusted under 35 U.S.C. 154(b) by 18 days.

This patent is subject to a terminal disclaimer.

(21) Appl. No.: 17/933,950

(22) Filed: Sep. 21, 2022

(65) Prior Publication Data

US 2023/0111536 A1    Apr. 13, 2023

Related U.S. Application Data

(63) Continuation of application No. 16/736,004, filed on Jan. 7, 2020, now Pat. No. 11,478,641, which is a
(Continued)

(51) Int. Cl.
*A61N 1/36*    (2006.01)
*A61B 17/34*    (2006.01)
(Continued)

(52) U.S. Cl.
CPC ........ *A61N 1/3605* (2013.01); *A61B 17/3468* (2013.01); *A61N 1/0526* (2013.01);
(Continued)

(58) Field of Classification Search
CPC .. A61N 1/3605; A61N 1/0526; A61N 1/0551; A61N 1/36075; A61N 1/37205; A61B 17/3468
See application file for complete search history.

(56) References Cited

U.S. PATENT DOCUMENTS 9,220,524 B2    12/2015    Boling et al.
9,456,836 B2    10/2016    Boling et al.
(Continued)

OTHER PUBLICATIONS

PCT International Search Report and Written Opinion for corresponding International Application Serial No. PCT/US2016/065757, pp. 1-16, dated Mar. 21, 2017.
(Continued)

*Primary Examiner* — Richard G Louis
(74) *Attorney, Agent, or Firm* — Stinson LLP

(57) ABSTRACT

One aspect of the present disclosure includes a delivery tool configured to deliver a neurostimulator into a pterygopalatine fossa of a subject. The neurostimulator can include a body connected to an integral stimulation lead having one or more stimulating electrodes. The delivery tool can comprise a handle, an elongated shaft extending from the handle, a hub portion, and a double barrel sheath. The hub portion can be located between the shaft and a spine member that extends axially away from the hub portion. The hub portion can be sized and dimensioned to releasably mate with the neurostimulator. The double barrel sheath can be connected to the spine member. A central lumen can extend through at least a portion of the shaft and the hub portion. The central lumen can be adapted to receive a lead ejector for selective deployment of the stimulation lead from the double barrel sheath.

7 Claims, 30 Drawing Sheets

Related U.S. Application Data continuation of application No. 15/373,698, filed on Dec. 9, 2016, now abandoned.

(60) Provisional application No. 62/265,086, filed on Dec. 9, 2015.

(51) Int. Cl.
  *A61N 1/05* (2006.01)
  *A61N 1/372* (2006.01)
(52) U.S. Cl.
  CPC ....... *A61N 1/0551* (2013.01); *A61N 1/36075* (2013.01); *A61N 1/37205* (2013.01)

(56) References Cited

U.S. PATENT DOCUMENTS

| | | | | |
|---|---|---|---|---|
| 2006/0136008 A1* | 6/2006 | Tadlock | ............... | A61N 1/0534 607/45 |
| 2010/0280585 A1* | 11/2010 | Appenrodt | ........... | A61N 1/0534 607/149 |
| 2012/0290057 A1* | 11/2012 | Boling | ................... | A61B 17/24 607/116 |

OTHER PUBLICATIONS

Assaf, A. T., et al. "Technical and surgical aspects of the sphenopalatine ganglion (SPG) microstimulator insertion procedure." International journal of oral and maxillofacial surgery 45.2 (2016): 245-254.

* cited by examiner

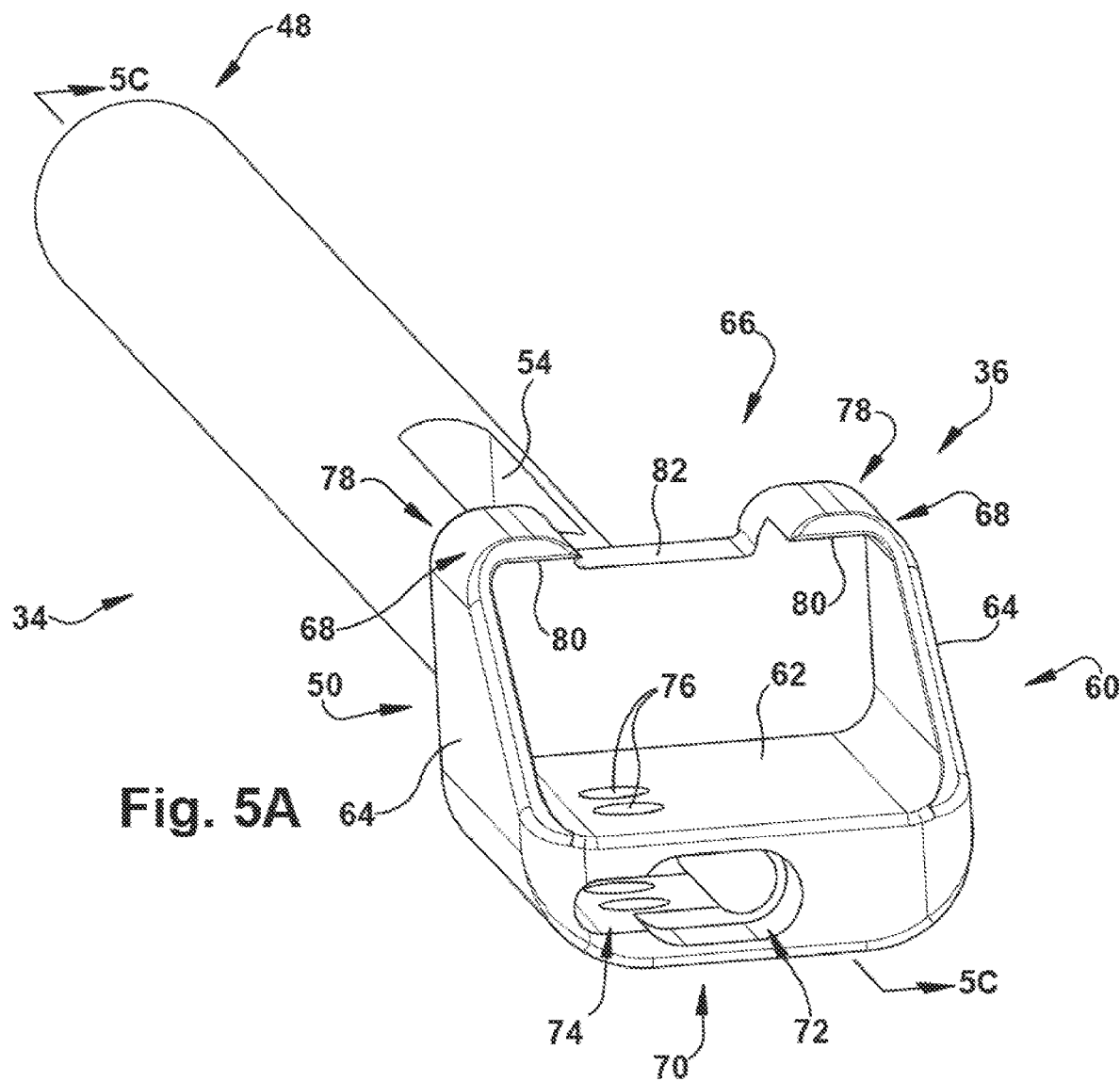

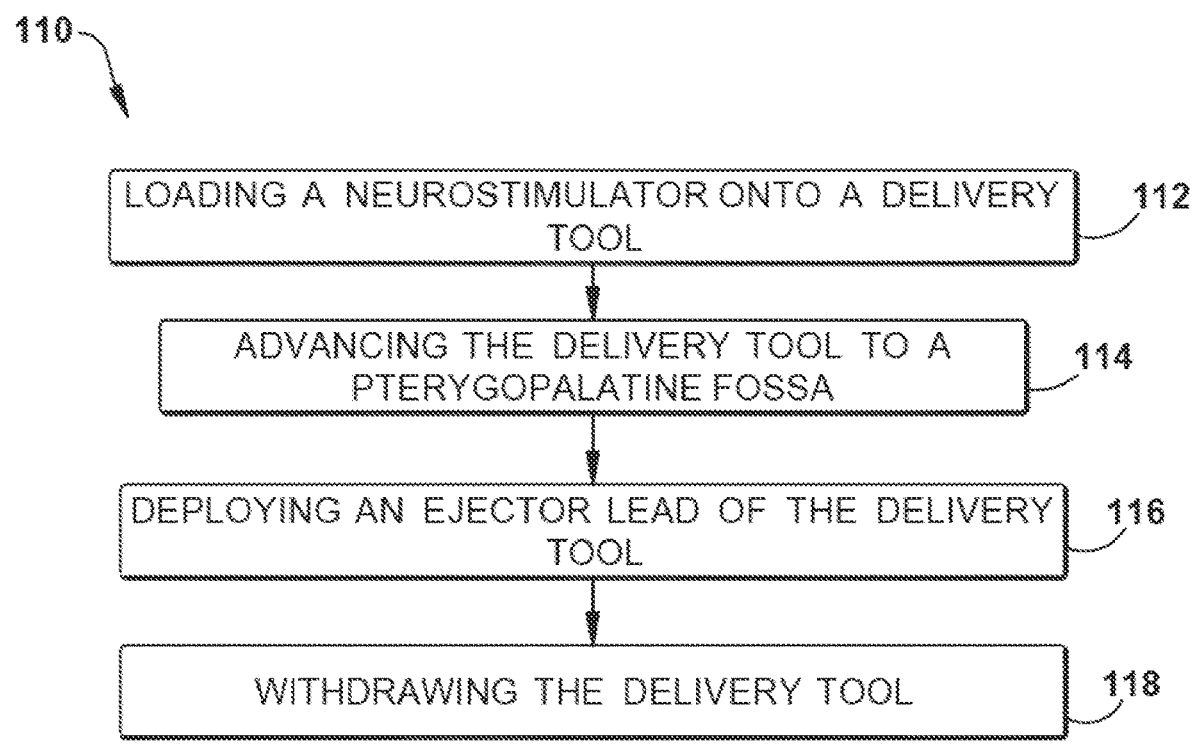

SURGICAL TOOLS AND METHODS FOR DELIVERING A NEUROSTIMULATOR INTO THE PTERYGOPALATINE FOSSA

RELATED APPLICATIONS

This application is a Continuation of U.S. patent application Ser. No. 16/736,004, filed Jan. 7, 2020, issued as U.S. Pat. No. 11,478,641, which is a Continuation of U.S. patent application Ser. No. 15/373,698, filed Dec. 9, 2016, which claims the benefit of U.S. Provisional Patent Application Ser. No. 62/265,086, filed Dec. 9, 2015, the entirety of each of which is hereby incorporated by reference for all purposes.

TECHNICAL FIELD

The present disclosure relates generally to surgical tools configured to deliver medical devices to a craniofacial region of a subject and, more particularly, to surgical tools configured to deliver an implantable neurostimulator to a pterygopalatine fossa of a subject.

BACKGROUND

Electrical stimulation of peripheral and central neural structures has shown increased interest due to the potential benefits it may provide to individuals suffering from many neurological and behavioral diseases. Many of these therapies today are not well accepted due to the invasive nature of the therapy, even though the efficacy is quite good. This has created a need for less invasive therapies that are directed toward patient and physician clinical needs.

Headaches are one of the most debilitating ailments that afflict millions of individuals worldwide. The specific pathophysiology of headaches is unknown. Known sources of headache pain consist of trauma, vascular, autoimmune, degenerative, infectious, drug and medication-induced, inflammatory, neoplastic, metabolic-endocrine, iatrogenic, musculoskeletal and myofacial causes. Also, even though the possible underlying cause of the headache pain is identified and treated, the headache pain may persist.

Currently, the sphenopalatine (pterygopalatine) ganglion (SPG) is a target of manipulation in clinical medicine to treat headaches. The SPG is an extracranial neuronal center located behind the nose. It consists of parasympathetic neurons that innervate (in part) the middle cerebral and anterior cerebral blood vessels, the facial blood vessels, and the lacrimal glands. The SPG also consists of sympathetic and sensory nerve fibers that pass through the SPG in route to their end organs. Manipulation of the SPG is mostly performed in attempted treatments of severe headaches, such as cluster headaches or migraines.

Various clinical approaches have been used for over 100 years to modulate the function of the SPG to treat headaches. These procedures vary from least invasive (e.g., transnasal anesthetic blocks) to much more invasive (e.g., surgical ganglionectomy), as well as procedures, such as surgical anesthetic injections, ablations, gamma knife and cryogenic surgery. These later procedures are very invasive, and most are non-reversible. In both cases, the surgical approach is typically through the nostrils or using a trans-coronoid notch approach.

SUMMARY

One aspect of the present disclosure includes a delivery tool configured to deliver a neurostimulator into a pterygopalatine fossa (PPF) of a subject. The neurostimulator can include a body connected to an integral stimulation lead having one or more stimulating electrodes. The delivery tool can comprise a handle, an elongated shaft extending from the handle, a hub portion, and a double barrel sheath. The hub portion can be located between the shaft and a spine member that extends axially away from the hub portion. The hub portion can be sized and dimensioned to releasably mate with the neurostimulator. The double barrel sheath can be connected to the spine member. A central lumen can extend through at least a portion of the shaft and the hub portion. The central lumen can be adapted to receive a lead ejector for selective deployment of the stimulation lead from the double barrel sheath.

Another aspect of the present disclosure includes a method for deploying a neurostimulator in close proximity to a sphenopalatine ganglion (SPG) of a subject. The neurostimulator can include a body connected to an integral stimulation lead having one or more stimulating electrodes. One step of the method can include loading the neurostimulator onto a delivery tool. The delivery tool can comprise a handle, an elongated shaft extending from the handle, a hub portion located between the shaft and a spine member that extends axially away from the hub portion, and a double barrel sheath connected to the spine member. At least a portion of the shaft and the hub portion can include a central lumen extending therethrough. Next, the delivery tool can be advanced so that the stimulation lead of the neurostimulator is adjacent a PPF of the subject. An ejector lead can then be deployed through the central lumen of the delivery tool to cause the stimulation lead to emerge from the double barrel sheath so that the stimulation lead is in close proximity to the SPG. The delivery tool can be withdrawn so that the neurostimulator remains implanted in the subject.

Another aspect of the present disclosure includes a navigation-compatible delivery tool configured to deliver a neurostimulator into a PPF of a subject. The neurostimulator can include a body connected to an integral stimulation lead having one or more stimulating electrodes. The delivery tool can comprise a handle, an elongated shaft extending from the handle, a hub portion located between the shaft and a trunk member that extends axially away from the hub portion, a spine member connected to and extending from the trunk member, and a double barrel sheath connected to the spine member.

Another aspect of the present disclosure includes a navigation-assisted method for deploying a neurostimulator in close proximity to a SPG of a subject. The neurostimulator can include a body connected to an integral stimulation lead having one or more stimulating electrodes. One step of the method can include loading the neurostimulator onto a delivery tool. The delivery tool can comprise a handle, an elongated shaft extending from the handle, a hub portion located between the shaft and a trunk member that extends axially away from the hub portion, a spine member connected to and extending from the trunk member, and a double barrel sheath connected to the spine member. Next, the tool can be advanced so that the stimulation lead of the neurostimulator is adjacent a PPF of the subject. The handle can be manipulated to cause a lead ejector of the delivery tool to displace the stimulation lead from the double barrel sheath so that the stimulation lead is in close proximity to the SPG. The delivery tool can then be withdrawn so that the neurostimulator remains implanted in the subject. The advancing, manipulating, and withdrawing steps can be performed using a navigation system.

BRIEF DESCRIPTION OF THE DRAWINGS

The foregoing and other features of the present disclosure will become apparent to those skilled in the art to which the present disclosure relates upon reading the following description with reference to the accompanying drawings, in which:

FIGS. 5A-B are perspective views of an elongated shaft and hub portion comprising the delivery tool in FIG. 3;

FIG. 8 is a process flow diagram illustrating a method for deploying a neurostimulator in close proximity to a sphenopalatine ganglion (SPG) of a subject according to another aspect of the present disclosure;

DETAILED DESCRIPTION

Figure 1:
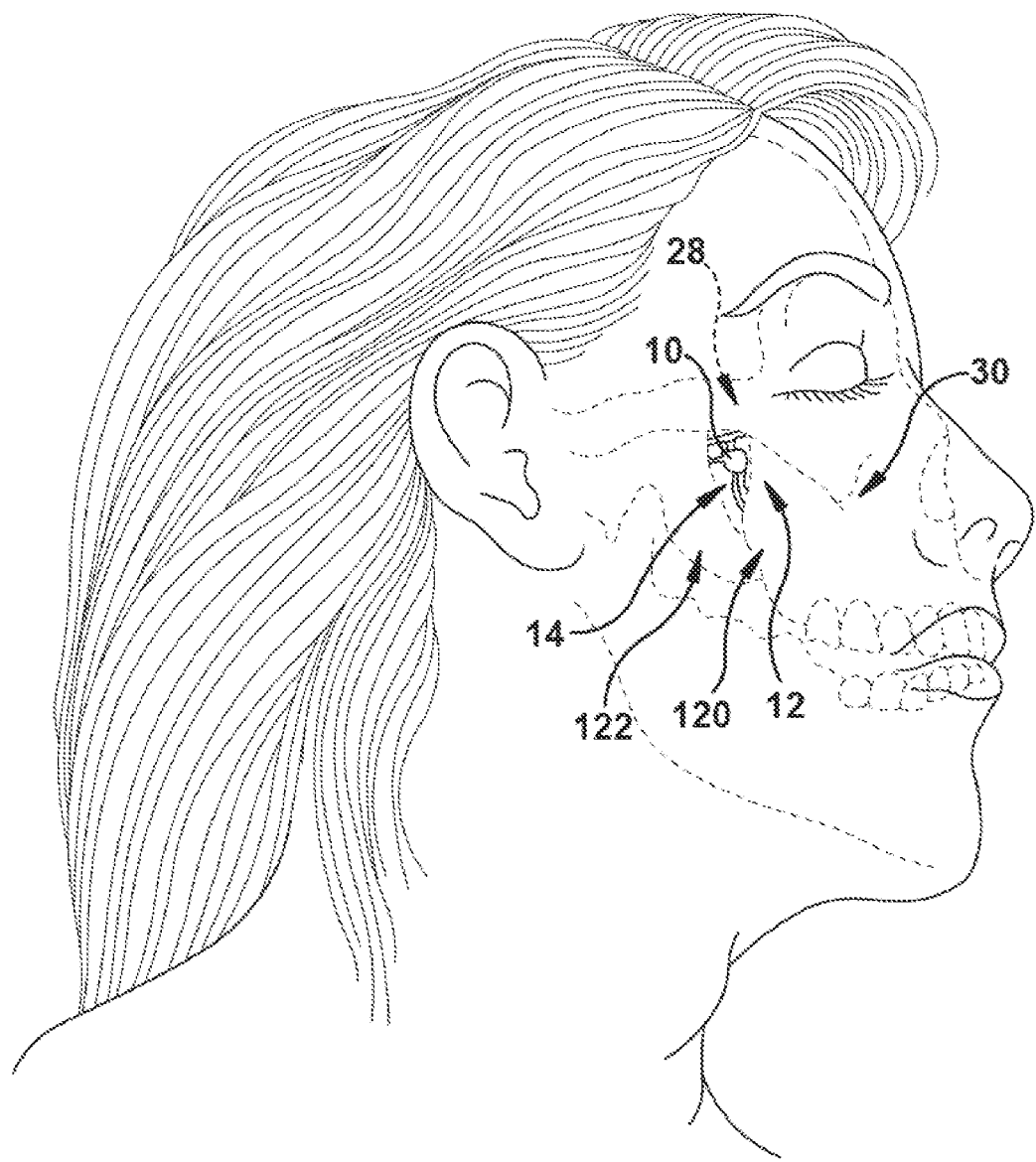
FIG. 1 is a perspective view showing part of the nervous innervations of the anterior craniofacial skeleton.

The present disclosure relates generally to surgical tools configured to deliver medical devices to a craniofacial region of a subject, and more particularly to surgical tools configured to deliver an implantable neurostimulator to a pterygopalatine fossa (PPF) of a subject. As described in more detail below, the delivery tools of the present disclosure are configured to deliver a neurostimulator into a craniofacial region of a subject, such as the PPF. The present disclosure may be employed to assist in treating a variety of chronic or acute medical conditions. Examples of such medical conditions can include, but are not limited to, pain (e.g., headache, facial pain, trigeminal neuralgias, sphenopalatine neuralgias and/or atypical face pain), movement disorders, epilepsy, cerebrovascular diseases, autoimmune diseases, sleep disorders, autonomic disorders, neurological disorders, urinary bladder disorders, abnormal metabolic states, disorders of the muscular system, and neuropsychiatric disorders.

Unless otherwise defined, all technical terms used herein have the same meaning as commonly understood by one of ordinary skill in the art to which the present invention pertains.

In the context of the present disclosure, the singular forms "a," "an" and "the" are intended to include the plural forms as well, unless the context clearly indicates otherwise. It will be further understood that the terms "comprises" and/or "comprising," as used herein, specify the presence of stated features, steps, operations, elements, and/or components, but do not preclude the presence or addition of one or more other features, steps, operations, elements, components, and/or groups thereof.

As used herein, the term "and/or" can include any and all combinations of one or more of the associated listed items.

As used herein, phrases such as "between X and Y" and "between about X and Y" should be interpreted to include X and Y.

As used herein, phrases such as "between about X and Y" can mean "between about X and about Y."

As used herein, phrases such as "from about X to Y" can mean "from about X to about Y."

It will be understood that when an element is referred to as being "on," "attached" to, "connected" to, "coupled" with, "contacting," etc., another element, it can be directly on, attached to, connected to, coupled with or contacting the other element or intervening elements may also be present. In contrast, when an element is referred to as being, for example, "directly on," "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

Spatially relative terms, such as "under," "below," "lower," "over," "upper" and the like, may be used herein for ease of description to describe one element or feature's relationship to another element(s) or feature(s) as illustrated in the figures. It will be understood that the spatially relative terms can encompass different orientations of the apparatus in use or operation in addition to the orientation depicted in the figures. For example, if the apparatus in the figures is inverted, elements described as "under" or "beneath" other elements or features would then be oriented "over" the other elements or features.

It will be understood that, although the terms "first," "second," etc. may be used herein to describe various elements, these elements should not be limited by these terms. These terms are only used to distinguish one element from another. Thus, a "first" element discussed below could also be termed a "second" element without departing from the teachings of the present disclosure. The sequence of operations (or steps) is not limited to the order presented in the claims or figures unless specifically indicated otherwise.

As used herein, the term "headache" can refer to migraines, tension headaches, cluster headaches, trigeminal neuralgia, sphenopalatine neuralgia, secondary headaches, tension-type headaches, chronic and episodic headaches, medication overuse/rebound headaches, chronic paroxysmal hemicrinia headaches, hemicranias continua headaches, post-traumatic headaches, post-herpetic headaches, vascular headaches, reflex sympathetic dystrophy-related headaches, cervicalgia headaches, caroidynia headaches, sciatica headaches, trigeminal headaches, occipital headaches, maxillary headaches, chary headaches, paratrigeminal headaches, petrosal headaches, Sluder's headache, vidian headaches, low cerebrospinal fluid pressure headaches, temporomandibular joint (TMJ) headaches, causalgia headaches, myofascial headaches, all primary headaches (e.g., primary stabbing headache, primary cough headache, primary exertional headache, primary headache associated with sexual activity, hypnic headache, and new daily persistent headache), all trigeminal autonomic cephalagias (e.g., paroxysmal hemicranias, short-lasting unilateral neuralgiform headache attacks with conjunctival injection and tearing (SUNCT) and short-lasting unilateral neuralgiform headache attacks with cranial autonomic symptoms (SUNA)), chronic daily headaches, occipital neuralgia, atypical facial pain, neuropathic trigeminal pain, and miscellaneous-type headaches.

As used herein, the term "cluster headache" can refer to extremely painful and debilitating headaches that occur in groups or clusters. Cluster headaches can include chronic or episodic cluster headaches, cluster-type headaches, histamine headaches, histamine cephalalgia, Raedar's syndrome and sphenopalatine neuralgia.

As used herein, the term "migraine" can refer to an intense and disabling chronic or episodic headache typically characterized by severe pain in one or both sides of the head. Migraines can include, but are not limited to, migraine without aura, migraine with aura, migraine with aura but without headache, menstrual migraines, variant migraines, transformed migraines, menstrual migraine, complicated migraines, hemiplegic migraines, atypical migraines, chronic migraines, basilar-type migraines, childhood periodic syndromes that are commonly precursors of migraine (e.g., abdominal, cyclic vomiting, BPV, etc.), status migrainous, and all types of probable migraines.

As used herein, the term "facial pain" can refer to direct pain that typically involves nerves supplying the face or, alternatively, indirect (referred) pain from other structures in the head, e.g., blood vessels. The pain may be related to headache (e.g., migraine), muscular syndromes (e.g., TMJ), and herpetic or rheumatic disease or injury.

As used herein, the terms "modulate" or "modulating" can refer to causing a change in neuronal activity, chemistry and/or metabolism. The change can refer to an increase, decrease, or even a change in a pattern of neuronal activity. The terms may refer to either excitatory or inhibitory stimulation, or a combination thereof, and may be at least electrical, biological, magnetic, optical or chemical, or a combination of two or more of these. The terms can also be used to refer to a masking, altering, overriding, or restoring of neuronal activity.

As used herein, the term "close proximity" with reference to a portion of an electrode or electrical lead relative to a target nerve structure (e.g., sphenopalatine ganglia or SPG) can refer to a distance between the electrode (or electrical lead) and the target nerve structure sufficient to enable electrical modulation of the target nerve structure. Thus, in some instances, "close proximity" can refer to a distance between the electrode (or electrical lead) and the target nerve structure whereby the electrode (or electrical lead) is not in direct contact with the nerve structure, but electrical modulation of the target nerve structure is still possible. In one example, "close proximity" can mean that the distance between an electrode or electrical lead and a target nerve structure is less than 1 mm but direct contact between structures does not occur. In another example, "close proximity" can mean that the distance between an electrode or electrical lead and a target nerve structure is greater than 1 mm (e.g., about 1 mm to about 1 cm), but direct contact between structures does not occur.

As used herein, the term "subject" can refer to any warm-blooded organism including, but not limited to, human beings, pigs, rats, mice, dogs, goats, sheep, horses, monkeys, apes, rabbits, cattle, etc.

As used herein, the term "prevent" shall have its plain and ordinary meaning to one skilled in the art of pharmaceutical or medical sciences. For example, "prevent" can mean to stop or hinder a medical condition, such as a headache.

As used herein, the terms "treat" or "treating" shall have their plain and ordinary meaning to one skilled in the art of pharmaceutical or medical sciences. For example, "treat" or "treating" can mean to prevent or reduce a medical condition, such as a headache.

As used herein, the term "medical condition" can refer to pain, movement disorders, epilepsy, cerebrovascular diseases, autoimmune diseases, sleep disorders, autonomic disorders, urinary bladder disorders, abnormal metabolic states, disorders of the muscular system, infectious and parasitic diseases, neoplasms, endocrine diseases, nutritional and metabolic diseases, immunological diseases, diseases of the blood and blood-forming organs, mental disorders, diseases of the nervous system, diseases of the sense organs, diseases of the circulatory system, diseases of the respiratory system, diseases of the digestive system, diseases of the genitourinary system, diseases of the skin and subcutaneous tissue, diseases of the musculoskeletal system and connective tissue, congenital anomalies, certain conditions originating in the perinatal period, and symptoms, signs, and ill-defined conditions.

Pain treatable by the present invention can be caused by conditions including, but not limited to, migraine headaches, including migraine headaches with aura, migraine headaches without aura, menstrual migraines, migraine variants, atypical migraines, complicated migraines, hemiplegic migraines, transformed migraines, and chronic daily migraines, episodic tension headaches, chronic tension headaches, analgesic rebound headaches, episodic cluster headaches, chronic cluster headaches, cluster variants, chronic paroxysmal hemicranias, hemicrania continua, post-traumatic headache, post-traumatic neck pain, post-herpetic neuralgia involving the head or face, pain from spine fracture secondary to osteoporosis, arthritis pain in the spine, headache related to cerebrovascular disease and stroke, headache due to a vascular disorder, reflex sympathetic dystrophy, cervicalgia (which may be due to various causes including, but not limited to, muscular, discogenic or degenerative, including arthritic, posturally related or metastatic), glossodynia, carotidynia, cricoidynia, otalgia due to middle ear lesion, gastric pain, sciatica, maxillary neuralgia, laryngeal pain, myalgia of neck muscles, trigeminal neuralgia (sometimes also termed tic douloureux), post-lumbar puncture headache, low cerebro-spinal fluid pressure headache, TMJ joint disorder, atypical facial pain, ciliary neuralgia, paratrigeminal neuralgia (sometimes also termed Raeder's syndrome), petrosal neuralgia, Eagle's syndrome, idiopathic intracranial hypertension, orofacial pain, myofascial pain syndrome involving the head, neck and shoulder, chronic migraneous neuralgia, cervical headache, paratrigeminal paralysis, sphenopalatine ganglion neuralgia (sometimes also termed lower-half headache, lower facial neuralgia syndrome, Sluder's neuralgia and Sluder's syndrome), carotidynia, vidian neuralgia, causalgia, atypical odontalgia, cluster tic syndrome, geniculate neuralgia, glossopharyngeal neuralgia, occipital neuralgia and temporal arteritis and/or a combination of the above.

Movement disorders treatable by the present invention may be caused by conditions including, but not limited to, Parkinson's disease, cerebropalsy, dystonia, essential tremor and hemifacial spasms.

Epilepsy treatable by the present invention may be, for example, generalized or partial.

Cerebrovascular disease treatable by the present invention may be caused by conditions including, but not limited to, aneurysms, strokes, and cerebral hemorrhage.

Autoimmune diseases treatable by the present invention include, but are not limited to, multiple sclerosis.

Sleep disorders treatable by the present invention may be caused by conditions including, but not limited to, circadian rhythm disorders, sleep apnea and parasomnias.

Autonomic disorders treatable by the present invention may be caused by conditions including, but not limited to, gastrointestinal disorders, including but not limited to gastrointestinal motility disorders, nausea, vomiting, diarrhea, chronic hiccups, gastroesphageal reflux disease, and hypersecretion of gastric acid, autonomic insufficiency, autonomic instability, excessive epiphoresis, excessive rhinorrhea, and cardiovascular disorders including, but not limited, to cardiac dysrythmias and arrythmias, hypertension, carotid sinus disease, Holmes-adie syndrome, orthostatic hypotension, striatonigral degeneration, vasovagal syncope, lyme disease and autonomic instability.

Neurological disorders treatable by the inventive method may be caused by conditions including, but not limited to: hemifacial spasm, Melkersson-Rosenthal Syndrome and Parry-Romberg syndrome.

Urinary bladder disorders treatable by the present invention may be caused by conditions including, but not limited to, spastic or flaccid bladder.

Abnormal metabolic states treatable by the present invention may be caused by conditions including, but not limited to, hyperthyroidism or hypothyroidism.

Disorders of the muscular system treatable by the present invention can include, but are not limited to, muscular dystrophy, and spasms of the upper respiratory tract and face.

Neuropsychiatric or mental disorders treatable by the present invention may be caused by conditions including, but not limited to, depression, schizophrenia, bipolar disorder, and obsessive-compulsive disorder.

A brief discussion of the pertinent anatomy and neurophysiology is provided to assist the reader with understanding the present invention. The autonomic nervous system innervates numerous pathways within the human body and consists of two divisions: the sympathetic and the parasympathetic nervous systems. The sympathetic and parasympathetic nervous systems are antagonistic in their action, balancing the other system's effects within the body. The sympathetic nervous system (SNS) usually initiates activity within the body, preparing the body for action, while the parasympathetic nervous system (PNS) primarily counteracts the effects of the SNS.

The SPG 10 (FIG. 1) are located on both sides of the head. It shall be assumed for the following discussion of the present invention that reference is being made to the SPG 10 located on the left side of the head. The SPG 14 10 located behind the posterior maxilla 12 the PPF 14, posterior to the middle nasal turbinate (not shown in detail). The SPG 10 is part of the parasympathetic division of the autonomic nervous system; however, the SPG has both sympathetic and parasympathetic nerve fibers, as well as sensory and motor nerve fibers either synapsing within the ganglion (e.g., parasympathetic) or fibers that are passing through the ganglion and not synapsing (e.g., sympathetic, sensory and motor).

The parasympathetic activity of the SPG 10 is mediated through the greater petrosal nerve (not shown), while the sympathetic activity of the SPG is mediated through the deep petrosal nerve (not shown), which is essentially an extension of the cervical sympathetic chain (not shown). Sensory sensations generated by or transmitted through the SPG 10 include, but are not limited to, sensations to the upper teeth, feelings of foreign bodies in the throat, and persistent itching of the ear. The SPG 10 transmits sensory information, including pain, to the trigeminal system via the maxillary division (not shown).

One aspect of the present disclosure includes a delivery tool 16 (FIG. 3) configured to deliver a neurostimulator into a craniofacial region of a subject. In some instances, the neurostimulator can be configured for implantation in the PPF 14. In other instances, the neurostimulator is sized and configured for implantation on a posterior maxilla 12. A neurostimulator capable of being delivered by the delivery tool 16 can generally include any active implantable medical device configured to deliver electrical stimulation, alone or in combination with other types of stimulation to tissue of a subject. The neurostimulator can further include any active implantable medical device configured for implantation for a relatively short period of time (e.g., to address acute medical conditions) or a relatively long period of time (e.g., to address chronic medical conditions). Additionally, the neurostimulator can include one or more elements used to record or monitor a physiological response of a subject's tissue (e.g., a delivered therapy), as well as one or more other components that interface with the patient's tissue (e.g., therapeutic agent delivery mechanisms, sensors, etc.).

Figure 2:
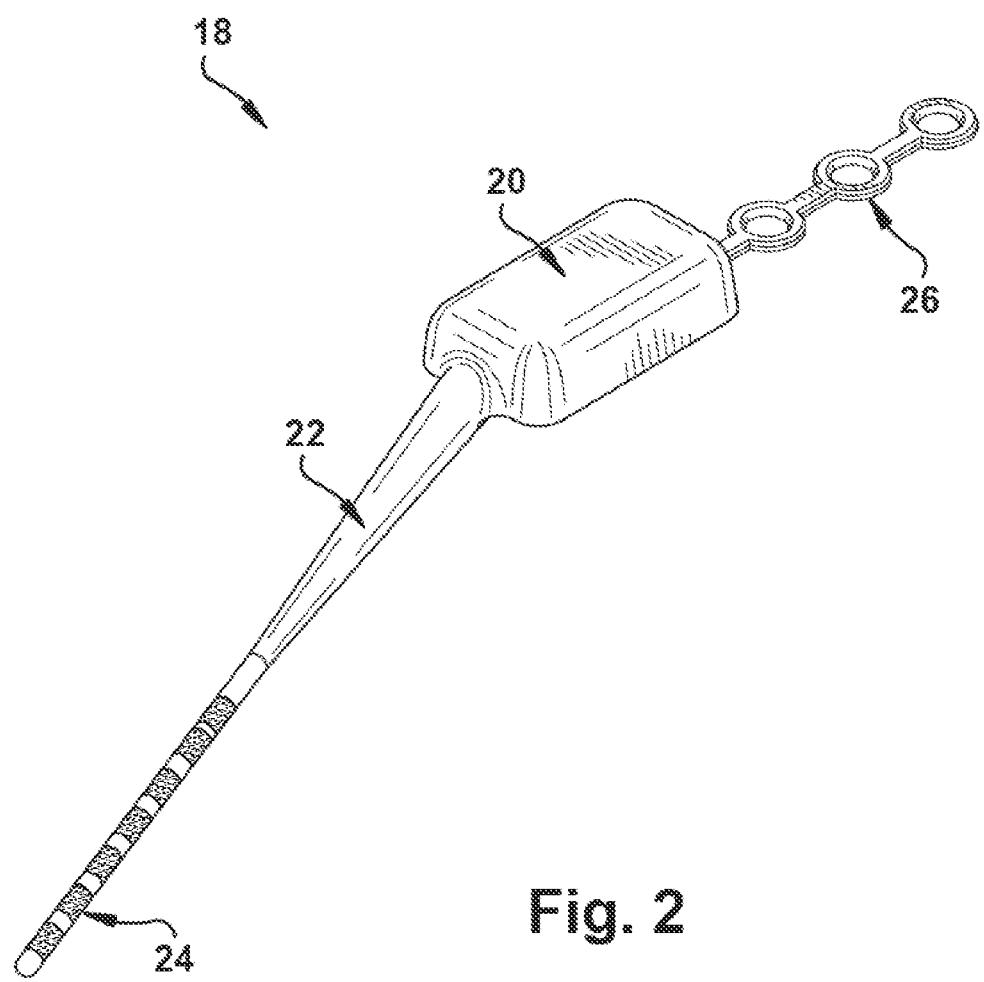
FIG. 2 is a perspective view of an implantable neurostimulator.

In one example of the present disclosure, a neurostimulator 18 can be configured as shown in FIG. 2 and disclosed in U.S. Pat. No. 8,494,641 to Boling et al. (hereinafter, "the '641 patent"), the entirety of which is hereby incorporated by reference. Briefly, the neurostimulator 18 can comprise a stimulator body 20, an integral stimulation lead 22, which includes one or more stimulating electrodes 24, and an integral fixation apparatus 26. The neurostimulator 18 can be implanted as disclosed in the '641 patent, i.e., such that the stimulator body 20 is positioned subperiosteally medial to the zygoma 28 (FIG. 1) on the posterior maxilla 12 within the buccal fat pad (not shown) of the cheek, and the integral fixation apparatus 26 (FIG. 2) is anchored to the zygomaticomaxillary buttress 30 (FIG. 1) such that the integral stimulation lead 22 (FIG. 2) is placed within the PPF 14 (FIG. 1) or, more specifically, in close proximity (e.g., about 1-5 mm) to the SPG 10.

Figure 3:
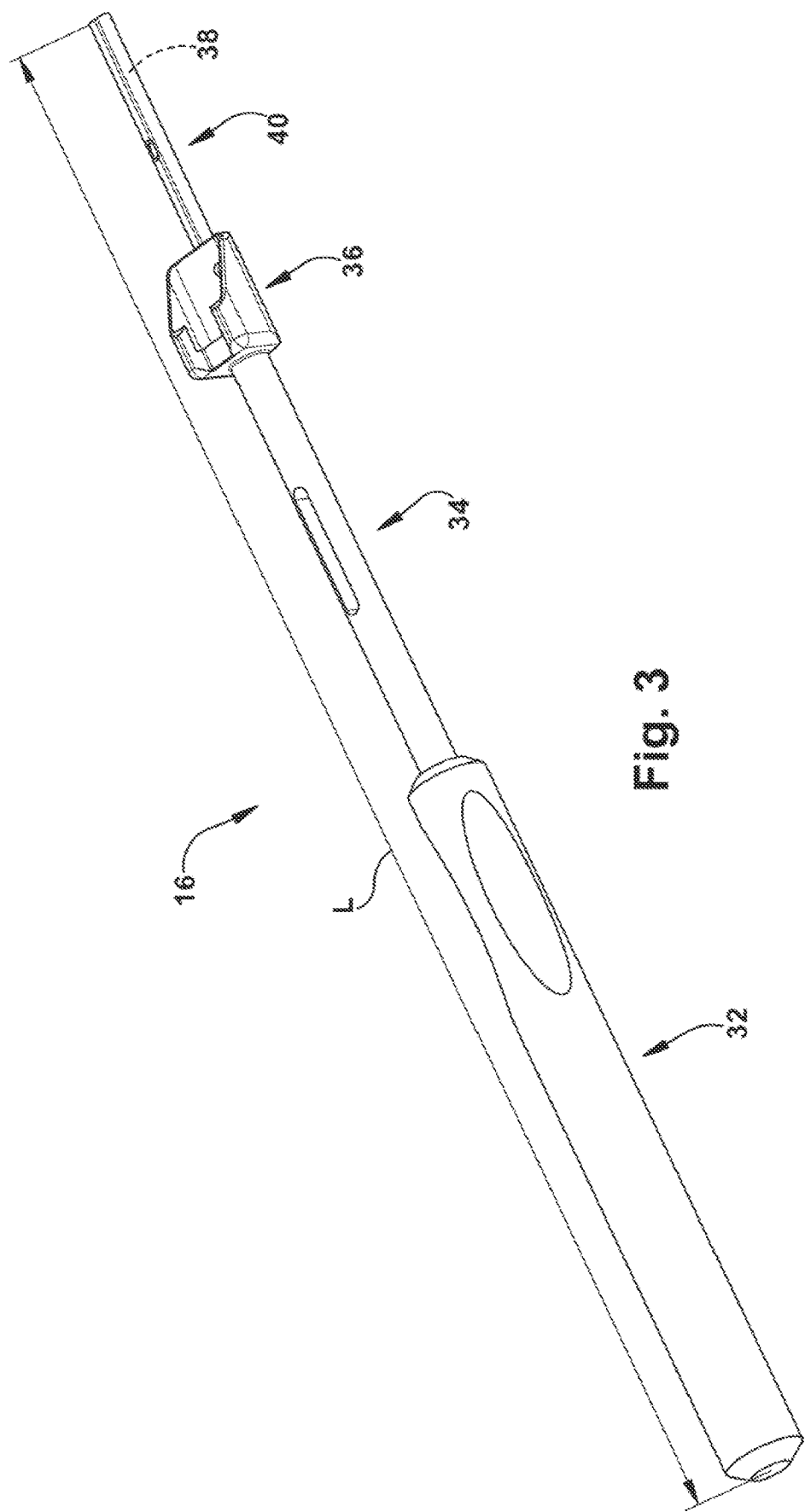
FIG. 3 is a schematic illustration of a delivery tool that is configured to deliver an implantable neurostimulator to a pterygopalatine fossa (PPF) of a subject and constructed in accordance with one aspect of the present disclosure.

The delivery tool 16 (FIG. 3) of the present disclosure is designed and configured to facilitate delivery of a neurostimulator in close proximity to the SPG 10 (FIG. 1) so that targeted electrical stimulation or delivery of electrical current from the neurostimulator to the SPG can be accomplished. Although reference below is made to the neurostimulator 18 in FIG. 2, it shall be appreciated that any variety of neurostimulator may be used as part of the present disclosure. Referring to FIG. 3, the delivery tool 16 can comprise a handle 32, an elongated shaft 34 extending from the handle, a hub portion 36 located between the shaft and a spine member 38, and a double barrel sheath 40 connected to the spine member. As described in more detail below, the delivery tool 16 is designed and configured to be inserted trans-orally from an incision located on the posterior maxilla 12 (FIG. 1).

In some instances, the delivery tool 16 (FIG. 3) can have a length L of about 10 cm to about 30 cm. In one example, the delivery tool 16 can have a length L of about 14 cm. All or only a portion of the delivery tool 16 can be made of a rigid or semi-rigid medical grade metal or metal alloy, such as titanium or stainless steel, medical grade plastics (e.g., PEEK, polycarbonate, nylon), glass, ceramics (e.g., aluminum, zirconium oxide), combinations of metals, ceramics, plastics or plastic composites, and the like.

Figure 4:
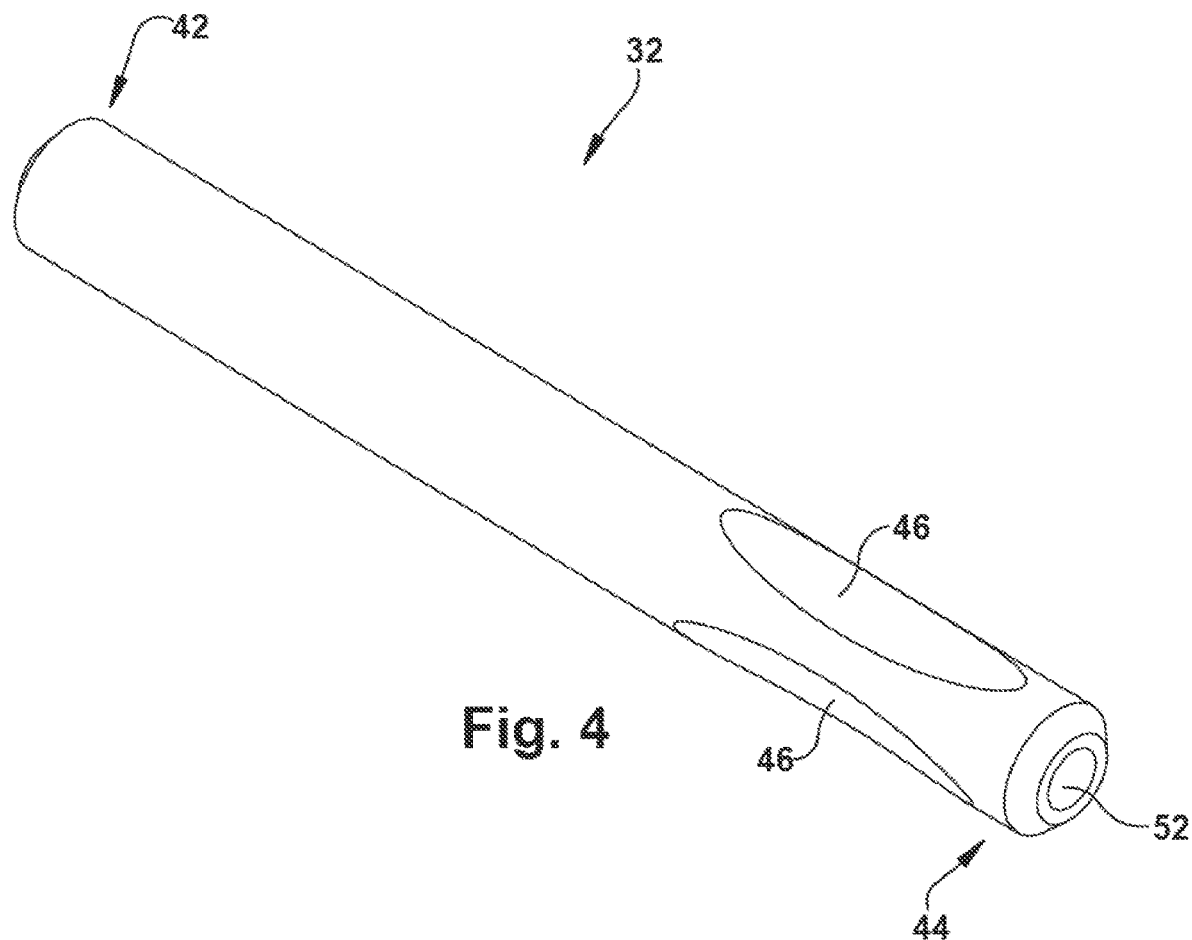
FIG. 4 is a perspective view of a handle comprising the delivery tool in FIG. 3.

In another aspect, the handle 32 can be ergonomically formed and have a length of about 6 cm to about 12 cm. The handle 32 can vary in diameter from a proximal end 42 (e.g., about 0.5 cm to about 3 cm) to a distal end 44 (e.g., about 0.5 cm to about 2 cm) thereof. The handle 32 can include various features to provide grip and tactile maneuverability, such as circumferential ridges or a cross-hatched precut pattern (not shown) into the material forming the handle. As shown in FIG. 4, the handle 32 can include a series of radially spaced apart depressions 46 (e.g., three) to provide a user with not only grip and tactile maneuverability, but also a visual cue to assist with proper positioning and orientation of the neurostimulator 18 during delivery. The handle 32 can be made of a rigid or semi-rigid medical grade metal or metal alloy, such as stainless steel, medical grade plastics, polymers, and the like.

In another aspect, the elongated shaft 34 (FIGS. 5A-C) of the delivery tool 16 includes oppositely disposed first and second end portions 48 and 50. The first end portion 48 is sized and dimensioned for insertion into a channel 52 of the handle 32. The second end portion 50 is securely connected to, or integrally formed with, the hub portion 36 of the delivery tool 16. The elongated shaft 34 can have any desired length and diameter. In some instances, the length of the elongated shaft 34 can be about 3 cm to about 7 cm. In one example, the length of the elongated shaft 34 can be about 4.5 cm. The diameter of the elongated shaft 34 can be about 0.1 cm to about 1 cm. In one example, the diameter of the elongated shaft 34 can be about 0.3 cm. In some instances, the diameter of the elongated shaft 34 can be uniform between the first and second end portions 48 and 50. In other instances, the diameter of the elongated shaft 34 can taper from the first end portion 48 to the second end portion 50 (or vice-versa). The elongated shaft 34 can be made of a rigid or semi-rigid medical grade metal or metal alloy, such as stainless steel, medical grade plastics, polymers, or the like.

Figure 5B:
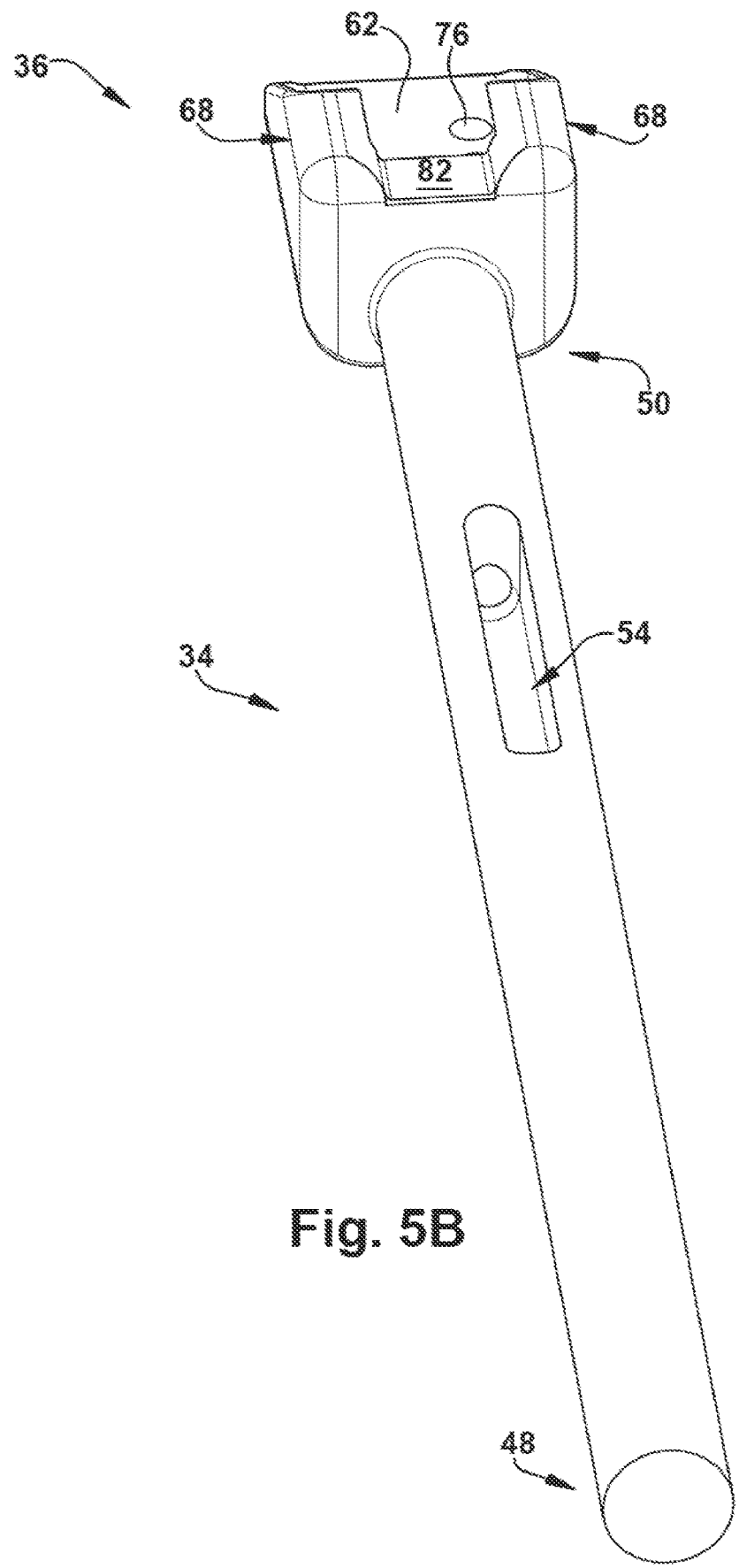
Figure 5C:
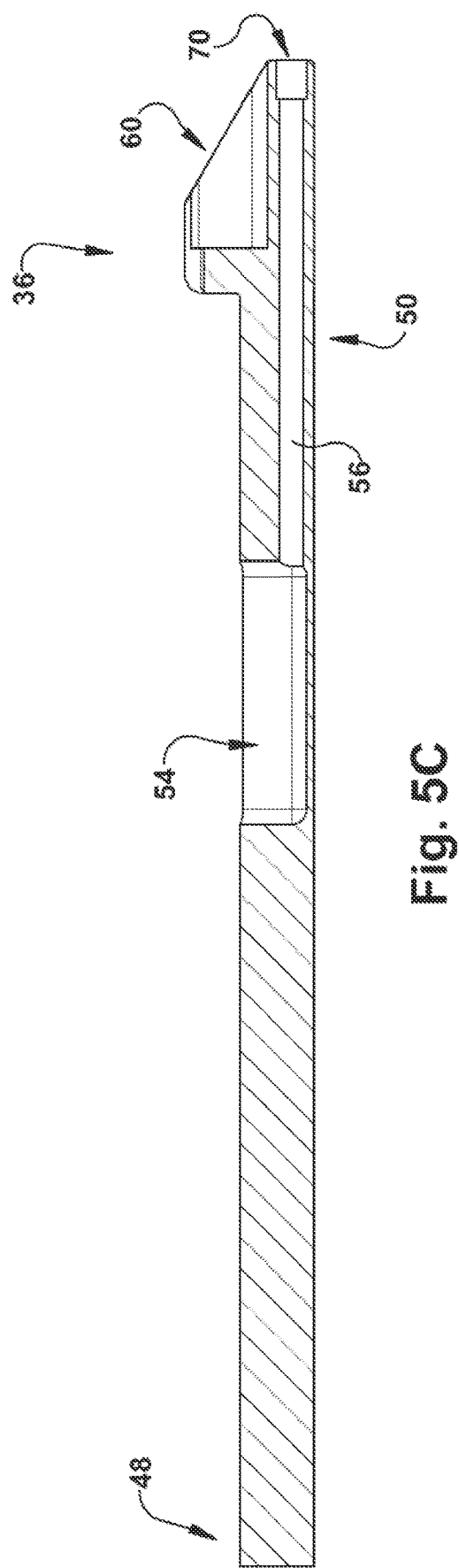
FIG. 5C is a cross-sectional view taken along Line 5C-5C in FIG. 5A.

The elongated shaft 34 also includes an opening or slot 54. The slot 54 can be located about any portion of the elongated shaft 34. In one example, the slot 54 is located at or about the middle of the elongated shaft 34. Although the slot 54 is shown in FIGS. 5A-C as having a rectangular shape, it will be appreciated that the slot can have any desired shape (e.g., circular, square, ovoid, etc.). The slot 54 forms part of a central lumen 56 (FIG. 5C), which extends through the elongated shaft 34 from the slot, through the second end portion 50, and through the hub portion 36. As described in more detail below, the slot 54 (and the central lumen 56) is adapted to receive an ejector lead 58 (FIGS. 9A-C) therethrough.

The hub portion 36 (FIGS. 5A-C) is located between the elongated shaft 34 and the spine member 38. The hub portion 36 is sized and configured to releasably mate with a neurostimulator 18. The hub portion 36 comprises a port 60 configured to slidably receive a stimulator body 20 of the neurostimulator 18. The port 60 is defined by a lower surface 62, which is integrally formed with oppositely disposed side walls 64, as well as an upper portion 66 that includes a plurality of tangs 68. Although not shown, it will be appreciated that the upper portion 66 can include only one tang 68.

As mentioned above, a portion of the central lumen 56 extends through the hub portion 36. The hub portion 36 thus includes a second opening 70 that is in fluid communication with the central lumen 56. The second opening 70 can be shaped like a bowling pin such that a first portion 72 thereof is adapted to receive the spine member 38, and a second portion 74 thereof is adapted to receive the double barrel sheath 40. The hub portion 36 can further include one or more channels 76 that extend from the lower surface 62 into the central lumen 56. The channel(s) 76 are sized and dimensioned to receive a fastener (not shown), such as a dowel to connect the spine member 38 to the hub portion 36. In one example, the hub portion 36 can include two channels 76 of identical diameter and length, each of which is adapted to receive a dowel.

The lower surface 62 can be sized and dimensioned to allow the hub portion 36 to releasably mate with the neurostimulator 18. In one example, the lower surface 62 can have a length of about 0.5 cm to about 2 cm (e.g., about 1 cm). In another example, the lower surface 62 can have a width of about 0.5 cm to about 2 cm (e.g., about 1 cm). Each of the oppositely disposed side walls 64 can have any desired height, such as about 0.1 cm to about 0.5 cm (e.g., about 0.3 cm). As shown in FIG. 5A, each of the side walls 64 can have a contoured arcuate portion 78.

The tangs 68, in addition to the lower surface 62 and the side walls 64 are configured to provide a retention force when the stimulator body 20 is received in the port 60. Each of the tangs 68 includes an overhang portion 80 for contacting a portion of the stimulator body 20 (e.g., when the neurostimulator 18 is disposed in the port 60). Each of the overhang portions 80 permits the amount of a retention force between the stimulator body 20 and the hub portion 36 to be selectively adjusted. For example, bending of the integral fixation apparatus 26 of the neurostimulator 18 towards a surface 82 of the upper portion 66 creates opposing forces between the overhang portions 80 and a surface of the stimulator body 20. Increasing an adjustment angle of the integral fixation apparatus 26 towards the surface 82 results in an increased retention force. Removal of the retention force during retraction requires the integral fixation apparatus 26 to be pushed away from the surface 82.

The hub portion 36 can be made of a rigid or semi-rigid medical grade metal or metal alloy, such as stainless steel, medical grade plastics, polymers, or the like. The hub portion 36 is configured to hold or carry the neurostimulator body 20 during placement of the neurostimulator 18. Thus, one skilled in the art will appreciate that the amount of material used to form the hub portion 36 should be minimized to reduce the amount of tissue dissection needed to place the neurostimulator 18 in vivo, as well as to reduce the amount of drag that occurs during placement and removal of the delivery tool 16.

Figure 6:
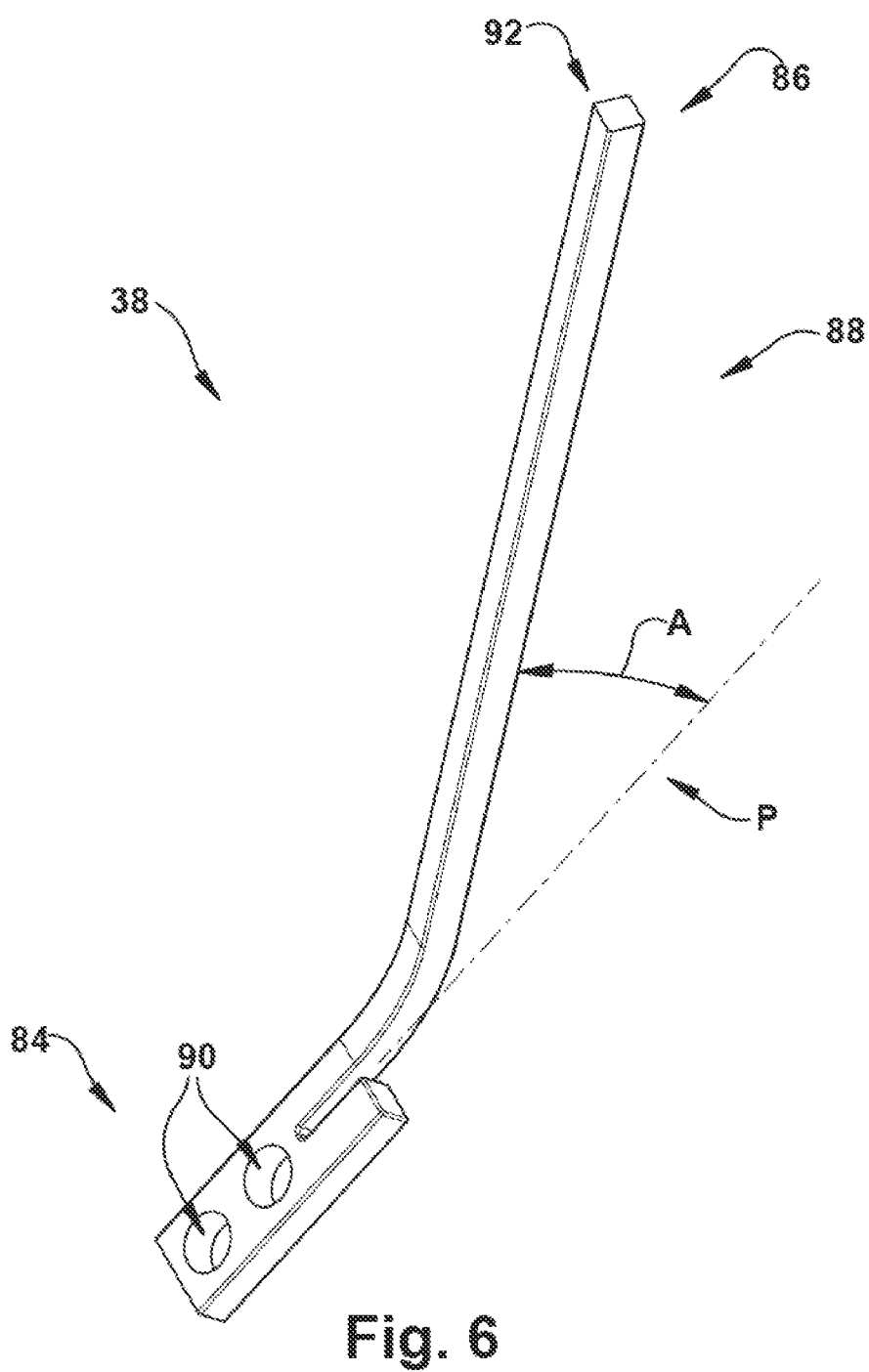
FIG. 6 is a perspective view of a spine member comprising the delivery tool in FIG. 3.

In another aspect, the spine member 38 (FIG. 6) extends axially away from, and is securely connected to, the hub portion 36. The spine member 38 has an elongated configuration and includes a proximal end portion 84, a distal end portion 86, and an intermediate portion 88 extending between the proximal and distal end portions. The proximal end portion 84 is adapted for connection to the hub portion 36 via one or more channel(s) 90, which is/are configured to receive a fastener, such as a dowel. In one example, the proximal end portion 84 can include two channels 90 of an identical diameter and length, each of which is adapted to receive a dowel.

The spine member 38 can have any desired length and width. In one example, the spine member 38 can have a length of about 4 cm to about 6 cm (e.g., about 5 cm). In another example, the spine member 38 can have a width of about 0.1 cm to about 0.8 cm (e.g., about 0.3 cm). The spine member 38 can have a uniform width or, alternatively, the width of the spine member can taper from a first width at the proximal end portion 84 that is greater than a second width at the distal end portion 86. In some instances, a distal tip 92 of the spine member 38 can include a tapered arcuate end. In other instances, the distal tip 92 can be bulbous or mushroom-shaped. In some instances, the spine member 38 can have a square-shaped cross-sectional profile; however, it will be appreciated that other cross-sectional profiles are possible (e.g., semi-circular, circular, rectangular, etc.).

In some instances, the distal end portion 86 of the spine member 38 can extend at an angle A relative to a longitudinal plane P of the proximal end portion 84. In one example, the angle A can be about 10° to about 45°, depending upon the craniofacial anatomy of the subject.

The spine member 38 can have a rigid, semi-rigid, or flexible configuration. The spine member 38 can be made from one or combination of rigid, semi-rigid, or flexible materials, such as metals, metal alloys, and polymers or plastics. In some instances, all or only a portion of the spine member 38 can be malleable. For example, only the distal end portion 86 of the spine member 38 can be malleable. In another example, the spine member 38 can be made of a malleable metal that supports the double barrel sheath 40 and the integral stimulation lead 22 from buckling when longitudinal or lateral forces are encountered. The malleability allows a physician to conform the shape of the neurostimulator 18 (e.g., the integral stimulation lead 22) to correspond to a patient's anatomy and thereby aid with implantation. Malleability in some cases is not required; thus, a spine member 38 made from a non-malleable material, such as plastic can also serve the intended function.

Figure 7A:
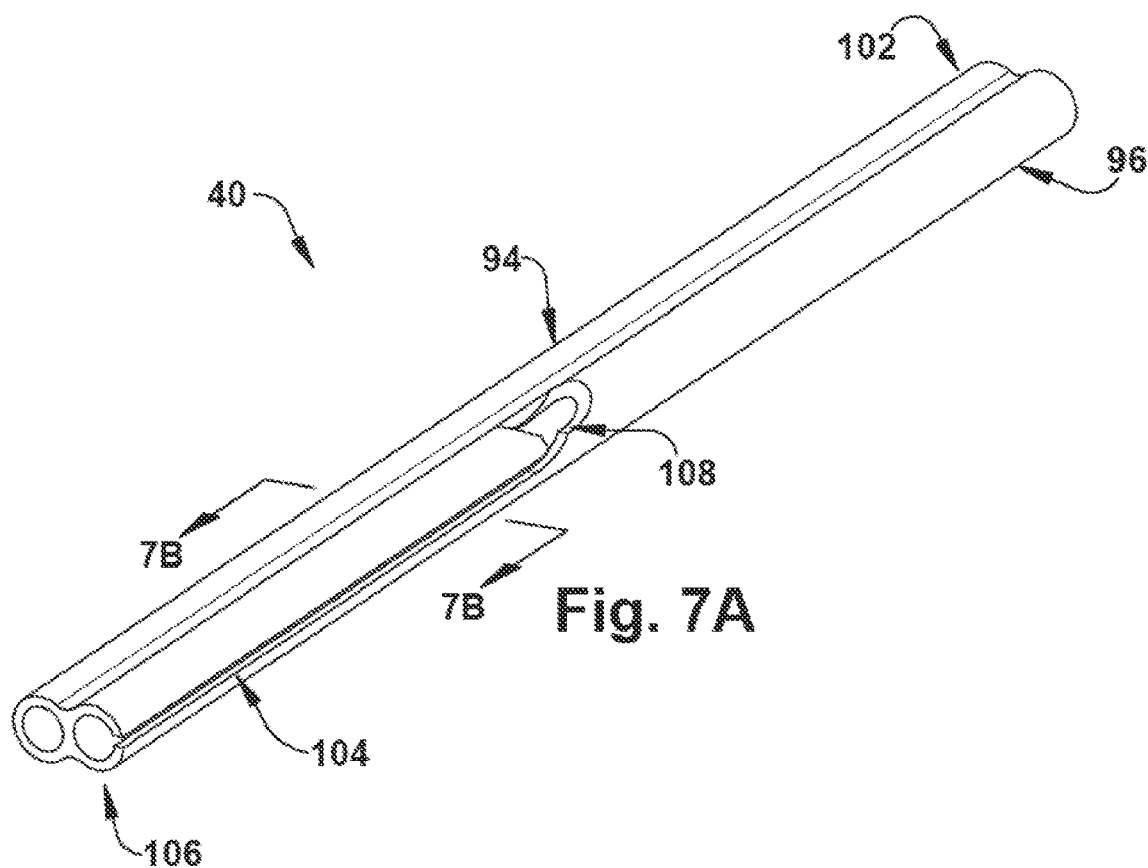
FIG. 7A is a perspective view of a double barrel sheath comprising the delivery tool in FIG. 3.
Figure 7B:
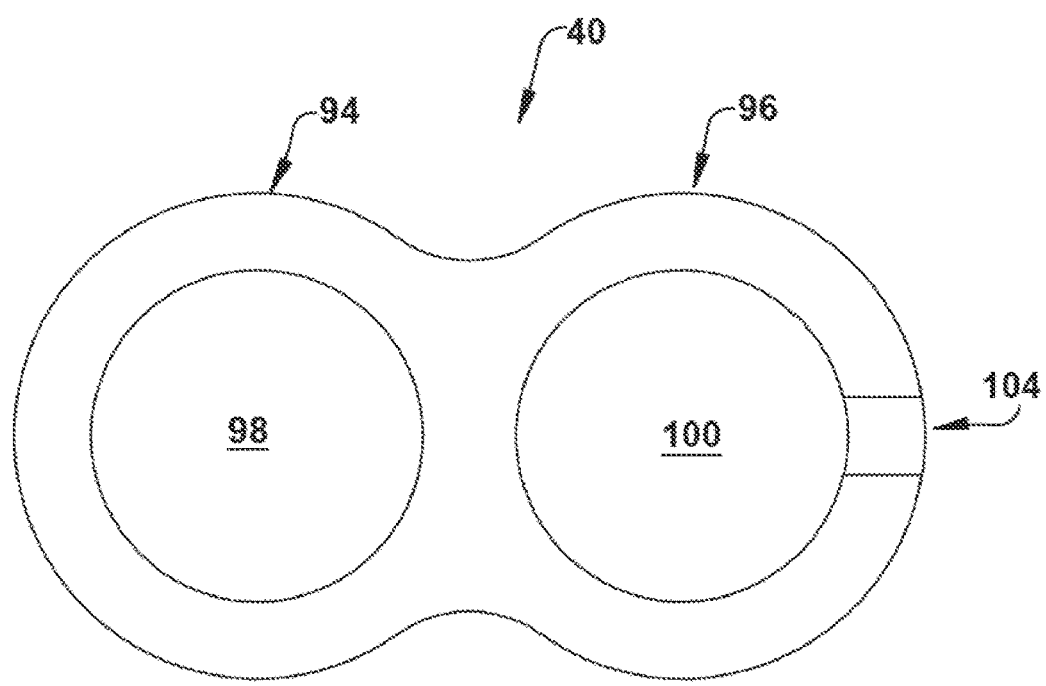
FIG. 7B is a cross-sectional view taken along Line 7B-7B in FIG. 7A.

In another aspect, the double barrel sheath 40 (FIGS. 7A-B) is connected to the spine member 38. The double barrel sheath 40 comprises a first barrel 94 and a second barrel 96. A first lumen 98 and a second lumen 100 extend through the first and second barrels 94 and 96, respectively. As shown in FIG. 7B, the double barrel sheath 40 can have an hour glass-like or figure eight-like cross-sectional profile. The first lumen 98 is shaped and dimensioned to receive the spine member 38. For example, all or only a portion of the spine member 38 can be disposed within the first lumen 98. In some instances, the spine member 38 is connected to an inner surface (not shown) defining the first lumen 98 by any one or combination of attachment mechanisms, such as adhesives, pins, staples, etc. The second lumen 100 is shaped and dimensioned to partially receive the integral stimulation lead 22 of the neurostimulator 18. A first end 102 of the double barrel sheath 40 is securely connected to the second opening 70 of the hub portion 36 such that the central lumen 56 is in fluid communication with the second lumen 100. The double barrel sheath 40 can be securely connected to the hub portion 36 by any one or combination of attachment mechanisms, such as adhesives, pins, staples, etc.

In some instances, the double barrel sheath 40 can be made of a semi-flexible material (or materials). In one example, the double barrel sheath 40 can be formed from a plastic or polymer, such as polytetrafluoroethylene. In other instances, the double barrel sheath 40 can be formed from a flexible material having a thickness of about 0.04 inches to about 0.001 inches.

In some instances, the second barrel 96 of the sheath 40 has a splittable configuration to allow for removal or deployment of the integral stimulation lead 22 of the neurostimulator 18 from the sheath with minimal load on the integral stimulation lead. A partial section of the second barrel 96 can include a seam 104 adapted to permit egress of the stimulation lead 22 from the second lumen 100 during deployment of the neurostimulator 18. The seam 104 can extend from a second end 106 of the sheath 40 to an opening 108, which is located at or about the midpoint of the second barrel 96. In some instances, the distance between the second end 106 and the opening 108 can be equal to, or about equal to, the length of the stimulation lead 22. The seam 104 allows for removal or deployment of the integral stimulation lead 22 of the neurostimulator 18 from the sheath 40 with minimal load on the integral stimulation lead. Undesirable loading on the integral stimulation lead 22 can cause migration of the lead away from the desired implant location during withdrawal of the delivery tool 16. Advantageously, only the seam 104 of the sheath 40 is parted during deployment of the neurostimulator 18, which reduces the load on the integral stimulation lead 22.

Another aspect of the present disclosure is illustrated in FIG. 8 and includes a method 110 for deploying a neurostimulator 18 in close proximity to a SPG 10 of a subject. The method 110 can generally include the steps of: loading a neurostimulator 18 onto a delivery tool (Step 112); advancing the delivery tool 16 to a PPF 14 (Step 114); deploying an ejector lead 58 of the delivery tool (Step 116); and withdrawing the delivery tool from the subject (Step 118). In one example of the method 110, the delivery tool 16 is configured as shown in FIG. 3 and described above, and the neurostimulator 18 is configured as shown in FIG. 2 and described in the '641 patent.

Figure 9A:
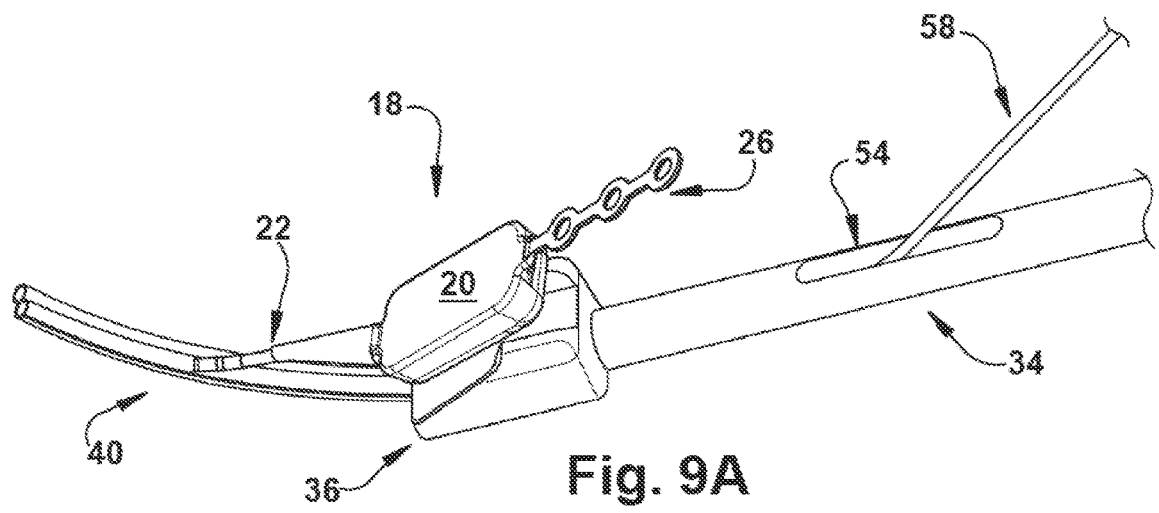
FIGS. 9A-C are a series of schematic illustrations showing loading of a neurostimulator onto the delivery tool in FIG. 3.
Figure 9B:
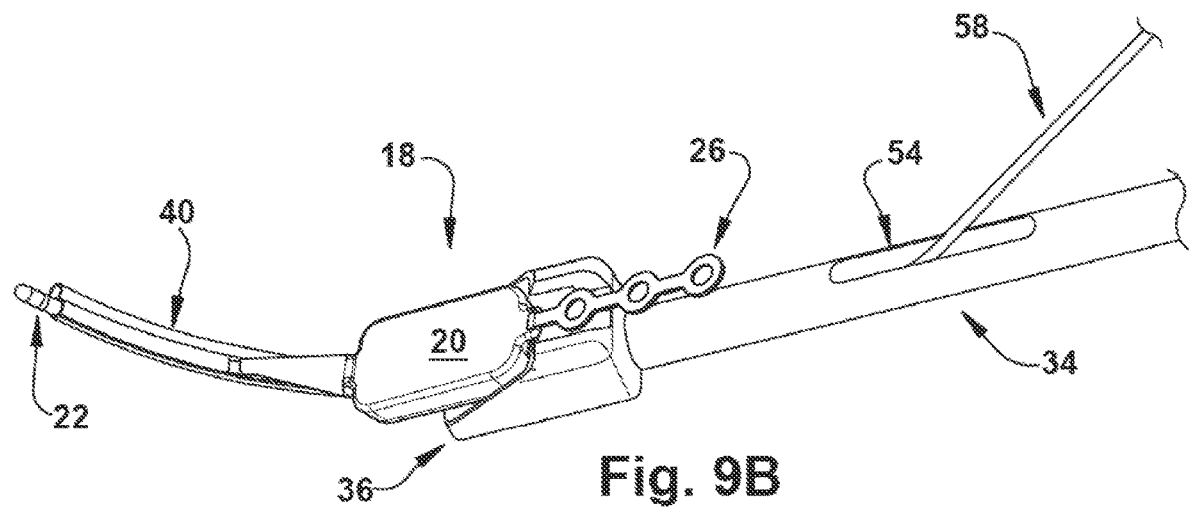
Figure 9C:
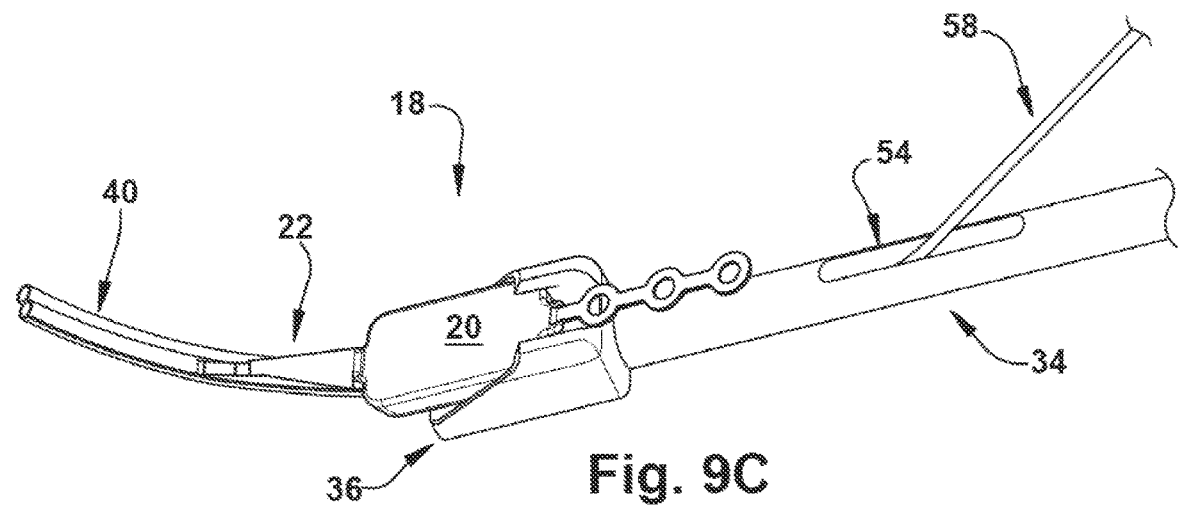

Either prior to, contemporaneous with, or following Step 112, a delivery path can be surgically formed in the subject as disclosed in U.S. patent application Ser. No. 13/470,480 (hereinafter, "the '480 application"), which is hereby incorporated by reference in its entirety. Loading of the neurostimulator 18 onto the delivery tool 16 is illustrated in FIGS. 9A-C. To do so, the neurostimulator 18 is first brought into close proximity with the hub portion 36 of the delivery tool 16. The neurostimulator 18 is then angled slight downward toward the double barrel sheath 40 of the delivery tool 16 until a distal portion of the integral stimulator lead 22 is introduced or inserted into the opening 108 of the sheath (FIG. 9A). Next, the neurostimulator 18 is progressively advanced in a distal direction until a portion of the neurostimulator body 20 is in flush contact with the lower surface 62 of the hub portion 36 (FIG. 9B). As shown in FIG. 9C, the neurostimulator 18 is then advanced towards the handle 32 of the delivery tool 16 until the neurostimulator body 20 snugly engages the tangs 68 and the integral fixation apparatus 26 engages the surface 82 of the hub portion 36, thereby providing a retention force to keep the neurostimulator securely mated with the delivery tool during implantation.

To form the delivery path, a gingival-buccal insertion site in a similar or identical manner as disclosed in U.S. Patent Publication No. 2010/0185258 A1 (hereinafter, "the '258 application"), which is hereby incorporated by reference in its entirety. In one example, a #10 scalpel blade (not shown) can be used to make an incision in a horizontal manner between the second and third molars (not shown). Next, a first surgical tool (not shown) similar or identical to the one disclosed in the '480 application is inserted into the incision and subperiosteally. In some instances, the anatomy of the subject's skull, including the location and size of the PPF 14 can be determined prior to insertion of the first surgical tool. After inserting the first surgical tool into the incision, the first surgical tool is urged in a posterior direction so that a first major surface of the surgical tool's distal portion traverses under the zygomatic bone 28 along the maxillary tuberosity 120. The first surgical tool is then advanced further until a distal dissecting tip thereof engages the junction formed by the posterior maxillary buttress (not shown) and the pterygoid plate 122, just inferior and lateral to the PPF 14. Advancement of the first surgical tool may naturally stop when the distal dissecting tip is correctly positioned at the junction formed by the posterior maxillary buttress and the pterygoid plate 122. The first surgical tool is then withdrawn, thereby creating a surgical access cavity (not shown).

After forming the delivery path, the delivery tool 16 (with the neurostimulator 18 loaded thereon) can be advanced through the delivery path until the stimulation lead 22 of the neurostimulator is adjacent the PPF 14 (Step 114). As shown in FIG. 9A, an ejector lead 58 is then inserted into the slot 54 of the delivery tool 16. In one example, the ejector lead 58 can comprise an electrode lead blank configured to have the same or substantially the same dimensions as the integral stimulation lead 22 of the neurostimulator 18. At Step 116, the ejector lead 58 can be progressively advanced through the slot 54 and the central lumen 56 to cause the stimulation lead 22 to emerge from the seam 104 of the double barrel sheath 40 so that the stimulation lead is in close proximity to the SPG 10.

At Step 118, the delivery tool 16 can be withdrawn so that the neurostimulator 18 remains implanted in the subject as disclosed in the '641 patent. Following completion of the surgery, and with the neurostimulator 18 securely implanted within the subject, an electrical current from the neurostimulator can be applied to the SPG 10 to treat a medical condition (e.g., headache).

Figure 10:
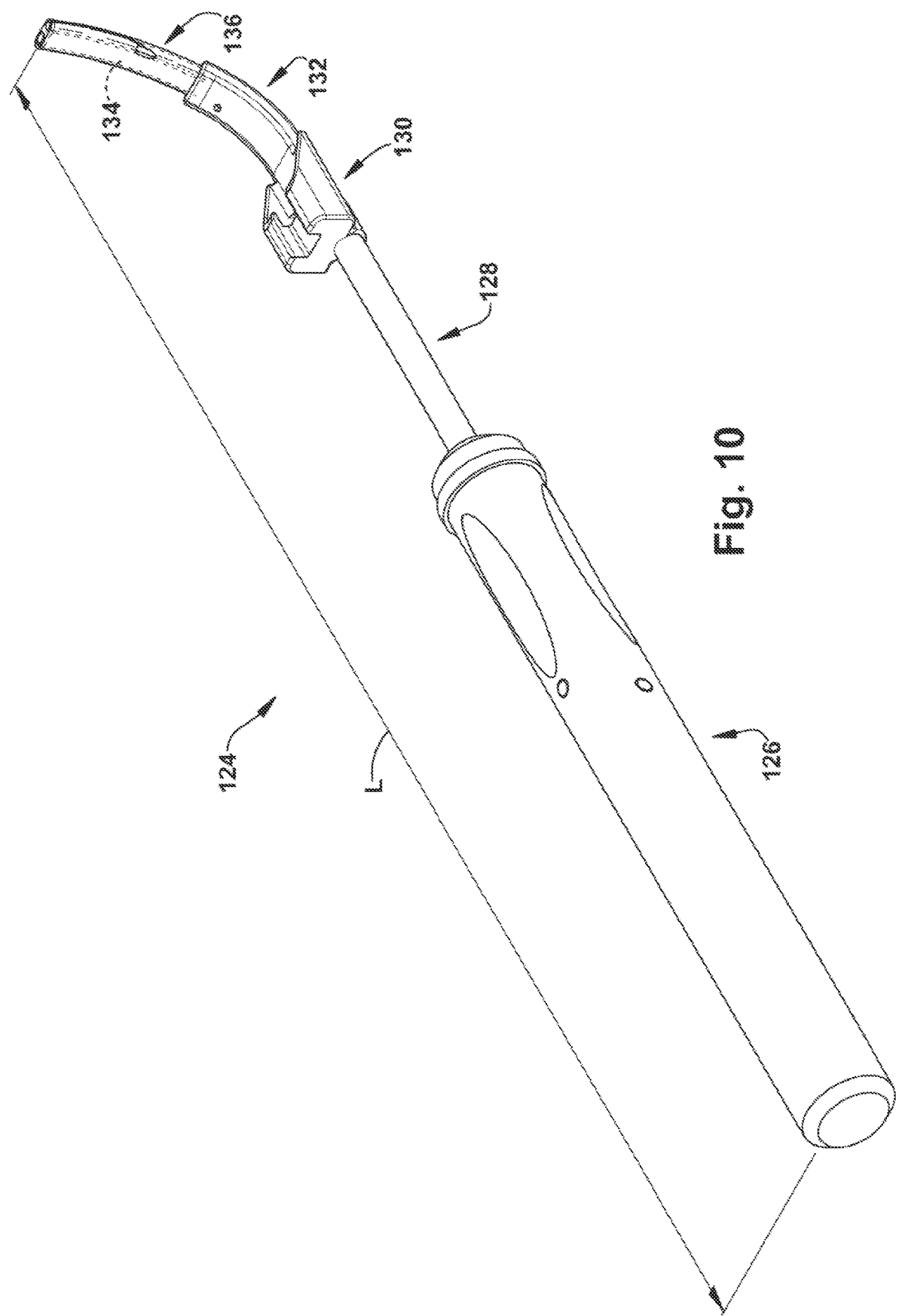
FIG. 10 is a schematic illustration of a delivery tool that is configured to deliver an implantable neurostimulator to a PPF of a subject and constructed in accordance with one aspect of the present disclosure.

In another aspect of the present disclosure, a navigation-compatible delivery tool 124 is illustrated in FIG. 10. The delivery tool 124 is configured to deliver, with navigation assistance, a neurostimulator into a craniofacial region of a subject. Non-limiting examples of navigation systems with which the delivery tool 124 is compatible can include those commercially available from BRAINLAB (Westchester, IL), such as the KICK or CURVE systems, the FUSION ENT navigation system (Medtronic, Minneapolis, MN), and the NAV3 Navigation Platform (Stryker, Kalamazoo, MI). In some instances, the neurostimulator can be configured for implantation in the PPF 14. In other instances, the neurostimulator is sized and configured for implantation on a posterior maxilla 12. A neurostimulator capable of being delivered by the delivery tool 124 can generally include any active implantable medical device configured to deliver electrical stimulation, alone or in combination with other types of stimulation to tissue of a subject. The neurostimulator can further include any active implantable medical device configured for implantation for a relatively short period of time (e.g., to address acute medical conditions) or a relatively long period of time (e.g., to address chronic medical conditions). Additionally, the neurostimulator can include one or more elements used to record or monitor a physiological response of a subject's tissue (e.g., a delivered therapy), as well as one or more other components that interface with the patient's tissue (e.g., therapeutic agent delivery mechanisms, sensors, etc.). One example of a neurostimulator 18 is shown in FIG. 2 and described above.

The delivery tool 124 of the present disclosure is designed and configured to facilitate delivery of a neurostimulator in close proximity to the SPG 10 so that targeted electrical stimulation or delivery of electrical current from the neurostimulator to the SPG can be accomplished. Although reference below is made to the neurostimulator 18 in FIG. 2, it shall be appreciated that any variety of neurostimulator may be used as part of the present disclosure. Referring to FIG. 10, the delivery tool 124 can comprise a handle 126, an elongated shaft 128 extending from the handle, a hub portion 130 located between the shaft and a trunk member 132 that extends axially away from the hub portion, a spine member 134 connected to and extending from the trunk member, and a double barrel sheath 136 connected to the spine member. As described in more detail below, the delivery tool 124 is designed and configured to be inserted trans-orally from an incision located on the posterior maxilla 12 (FIG. 1).

In some instances, the delivery tool 124 (FIG. 10) can have a length L of about 10 cm to about 30 cm. In one example, the delivery tool 124 can have a length L of about 14 cm. All or only a portion of the delivery tool 124 can be made of a rigid or semi-rigid medical grade metal or metal alloy, such as titanium or stainless steel, medical grade plastics (e.g., PEEK, polycarbonate, nylon), glass, ceramics (e.g., aluminum, zirconium oxide), combinations of metals, ceramics, plastics or plastic composites, and the like.

Figure 11A:
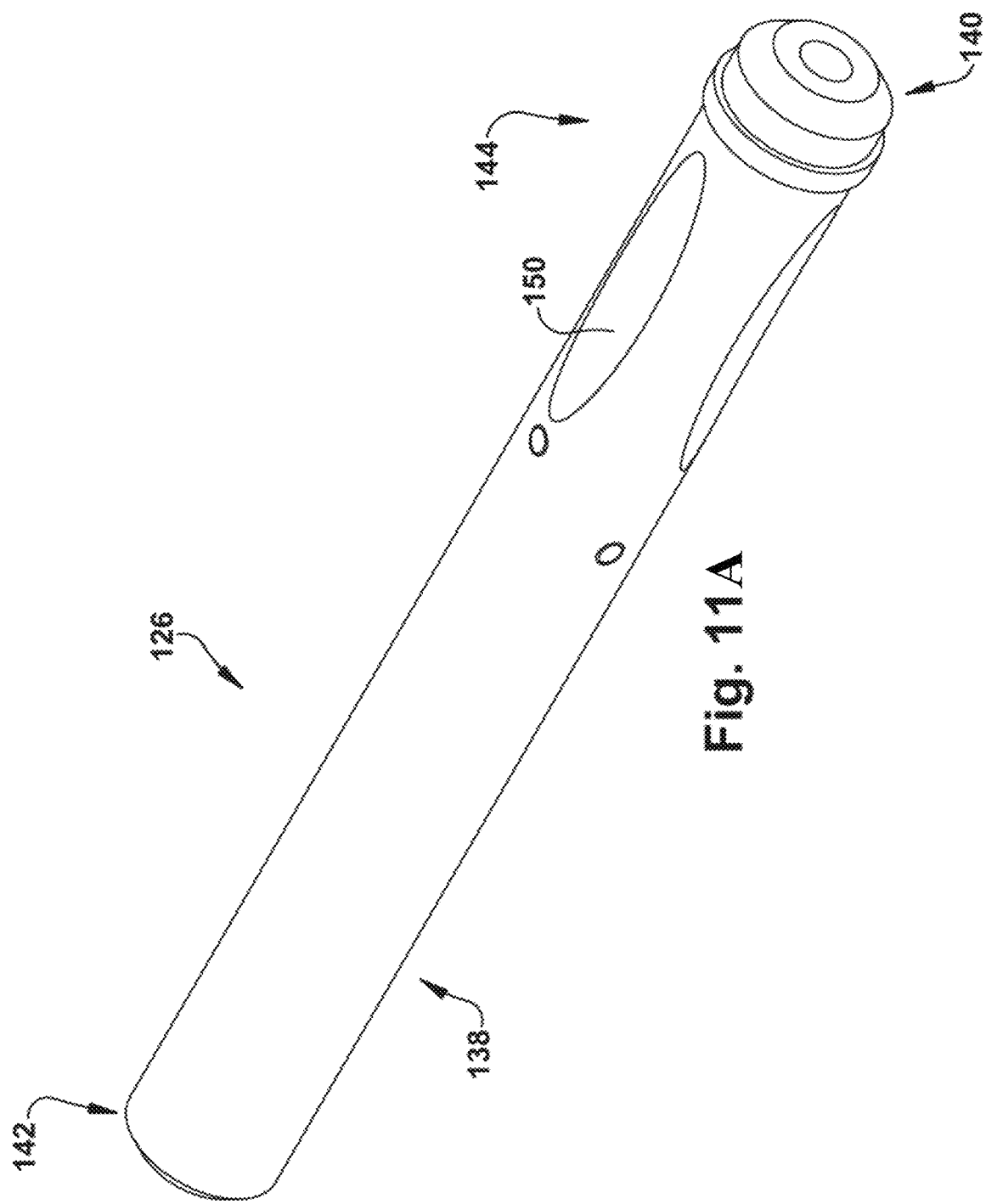
FIGS. 11A-B are perspective views of a handle comprising the delivery tool in FIG. 10 in an assembled configuration (FIG. 11A) and an exploded configuration (FIG. 11B)
Figure 11B:
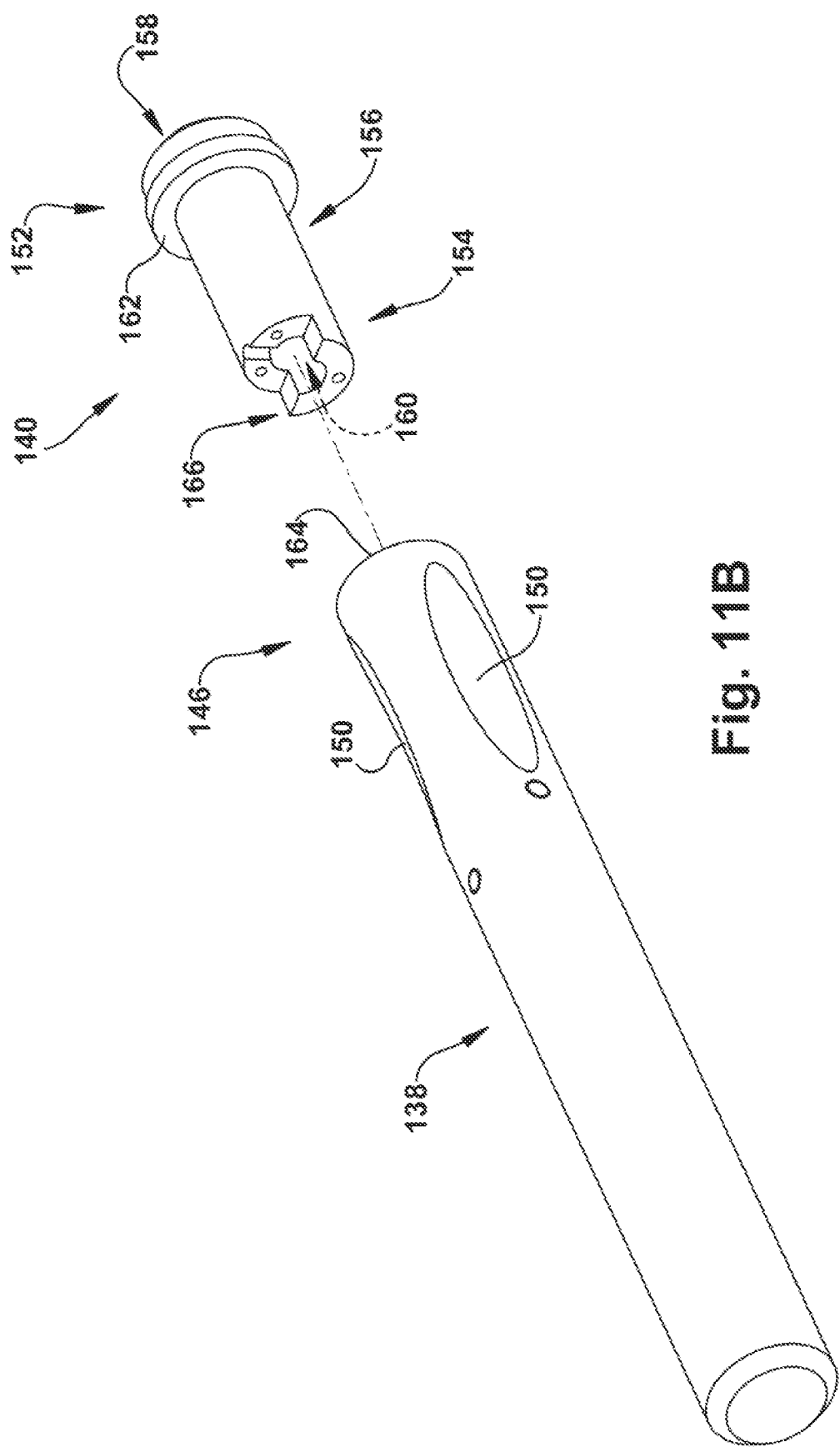

In another aspect, the handle 126 (FIGS. 11A-B) can be ergonomically shaped and comprise a first component 138 and a second component 140. The handle 126 can have a length of about 6 cm to about 12 cm. The handle 126 can vary in diameter from a proximal end 142 (e.g., about 0.5 cm to about 3 cm) to a distal end 144 (e.g., about 0.5 cm to about 2 cm) thereof. A first end portion 146 of the first component 138 can include a channel 148 adapted to receive a portion of the second component 140. The first component 138 can include various features to provide grip and tactile maneuverability, such as circumferential ridges or a cross-hatched precut pattern (not shown) into the material forming the handle. As shown in FIGS. 11A-B, the handle 126 can include a series of radially spaced apart depressions 150 (e.g., three) to provide a user with not only grip and tactile maneuverability, but also a visual cue to assist with proper positioning and orientation of the neurostimulator 18 during delivery. The first and second components 138 and 140 can be made of the same or different materials, such as a rigid or semi-rigid medical grade metal or metal alloy (e.g., stainless steel), medical grade plastics, polymers, and the like.

The second component 140 of the handle 126 can have a generally T-shaped configuration that includes a first end portion 152, a second end portion 154, and a main body 156 extending between the first and second end portions. The first end portion 152 comprises a cap member 158 having a diameter that is greater than a diameter of the main body 156 and the second end portion 154. A lumen 160 that is adapted to receive the elongated shaft 128 extends between the first and second end portions 152 and 154. The main body 156 and the second end portion 154 of the second component 140 can have a tubular or cylindrical shape, and be sized and dimensioned to fit within the channel 148 of the first component 138. When the second component 140 is received within the channel 148, an annular lip 162 comprising the cap member 158 can directly contact, and be flush with, a first end surface 164 of the first component 138. The second end portion 154 of the second component 140 also includes a step 166, which, as described in more detail below, forms part of an integral lead ejector mechanism of the delivery tool 124.

FIGS. 12A-G illustrate the integral lead ejector mechanism, which comprises the handle 126, the elongated shaft 128, a connector component 168, a plurality of fasteners 170, and an ejector lead 172. Unlike the delivery tool 16 described above, which requires tactile manipulation and insertion of the ejector lead 58 during operation, the ejector lead 172 of the delivery tool 124 is an integral component thereof and thereby obviates the need to externally feed an ejector lead into the delivery tool during neurostimulator deployment. Advantageously, the integral lead ejector mechanism reduces the time needed to implant a neurostimulator 18 and minimizes the potential for introducing contaminated equipment during a surgical procedure.

Figure 12A:
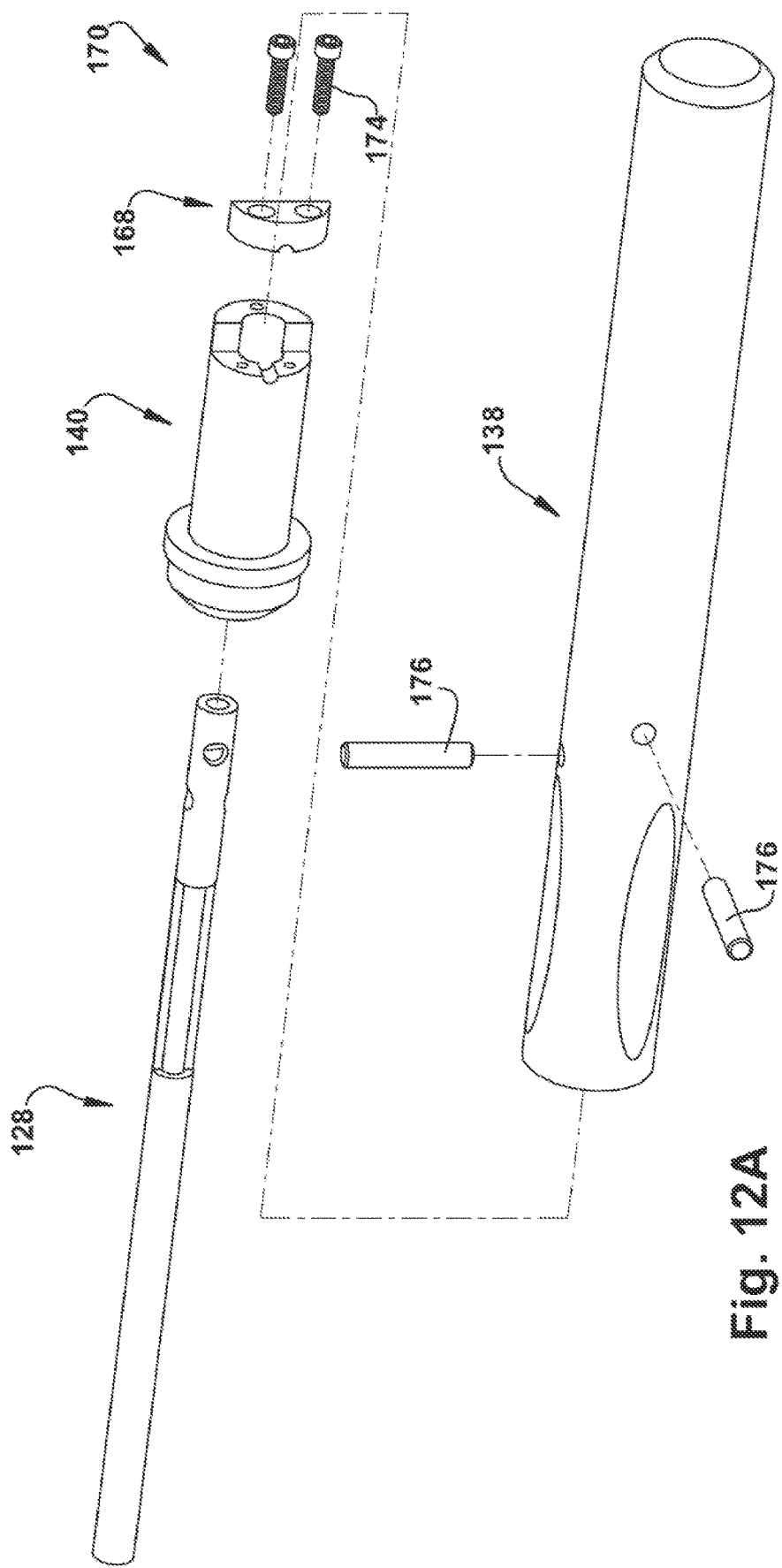
FIGS. 12A-G are a series of schematic illustrations showing an integral lead ejector mechanism of the delivery tool in FIG. 10.
Figure 12B:
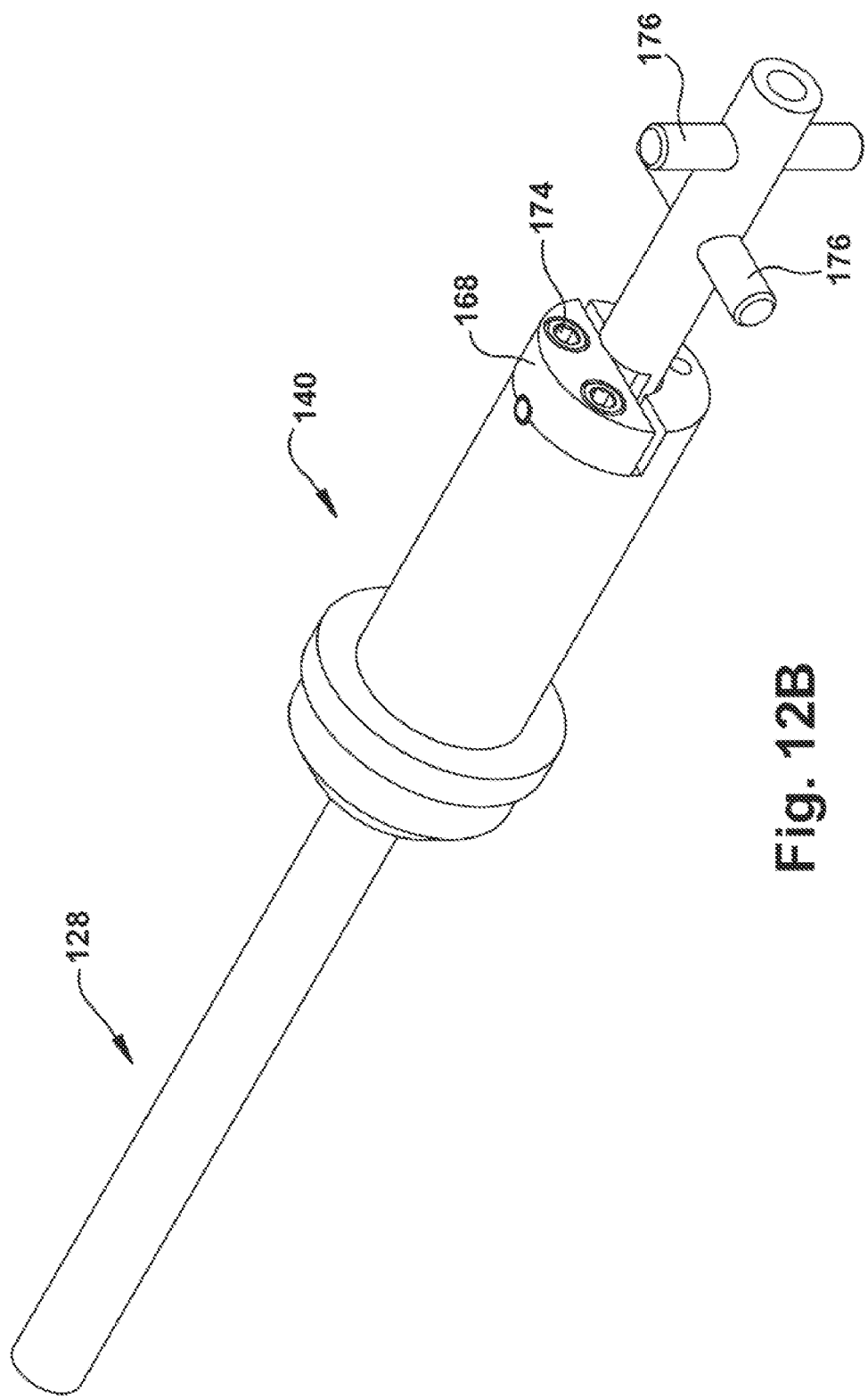

Referring to FIG. 12B, the elongated shaft 128 can extend through the second component 140 of the handle 126. The connector component 168 can be seated on the step 166 of the second component 140 and secured thereto by a plurality of screws 174. When the second component 140 and the elongated shaft 128 are mated as shown in FIG. 12B, a plurality of dowels 176 can extend through the first component 138 of the handle 126 into the elongated shaft to secure the elongated shaft in place.

In another aspect, the elongated shaft 128 (FIGS. 12C-D) includes oppositely disposed first and second end portions 178 and 180, and a central lumen 182 extending therebetween. The second portion 180 of the elongated shaft 128 is sized and dimensioned for insertion into the lumen 160 of the second component 140 of the handle 126. The first end portion 178 is securely connected to, or integrally formed with, the hub portion 130 of the delivery tool 124. The elongated shaft 128 can have any desired length and diameter. In some instances, the length of the elongated shaft 128 can be about 3 cm to about 7 cm. In one example, the length of the elongated shaft 128 can be about 4.5 cm. The diameter of the elongated shaft 128 can be about 0.1 cm to about 1 cm. In one example, the diameter of the elongated shaft 128 can be about 0.3 cm. In some instances, the diameter of the elongated shaft 128 can be uniform between the first and second end portions 178 and 180. The elongated shaft 128 can be made of a rigid or semi-rigid medical grade metal or metal alloy, such as stainless steel, medical grade plastics, polymers, or the like.

Figure 12C:
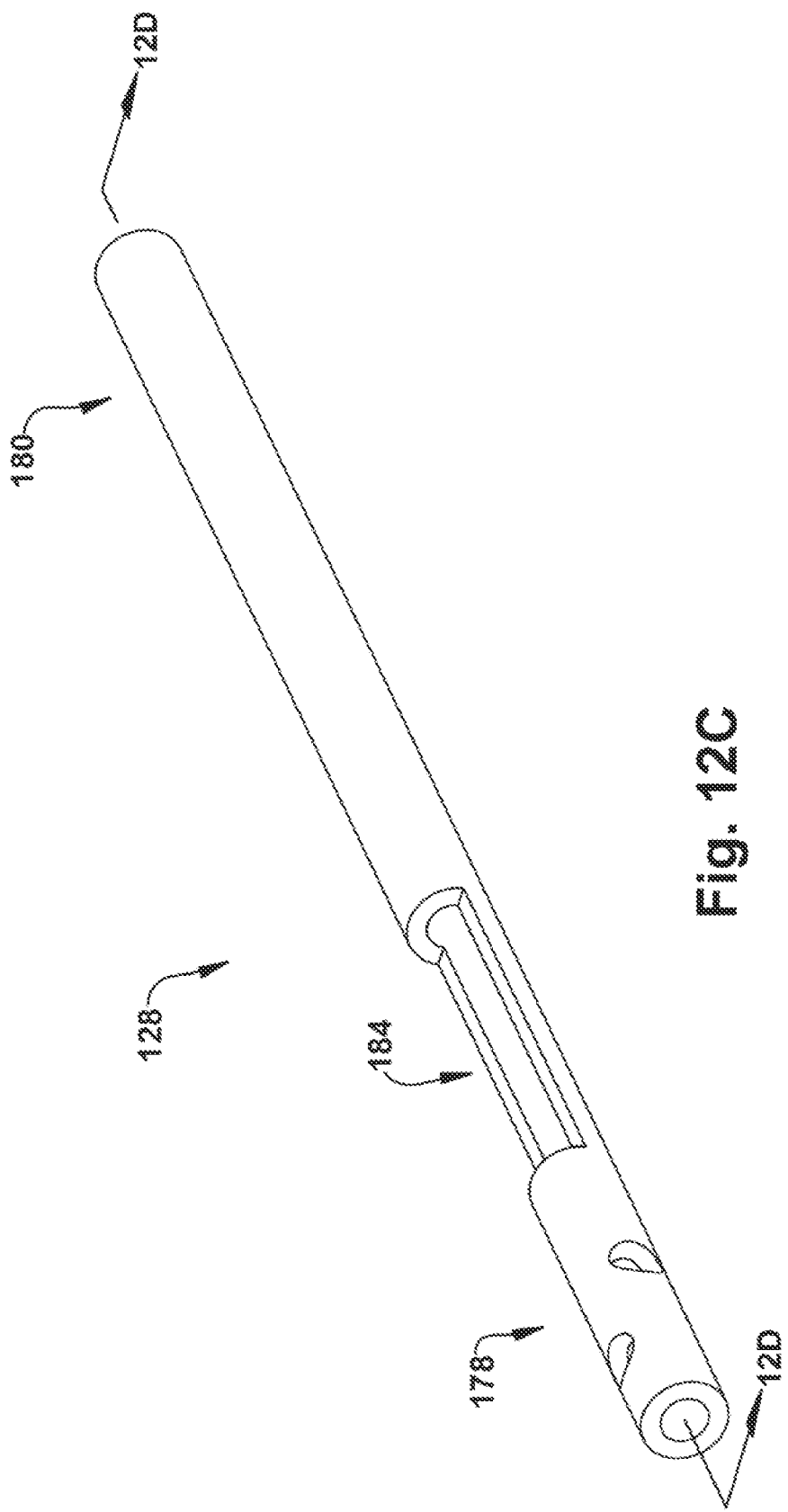
Figure 12D:
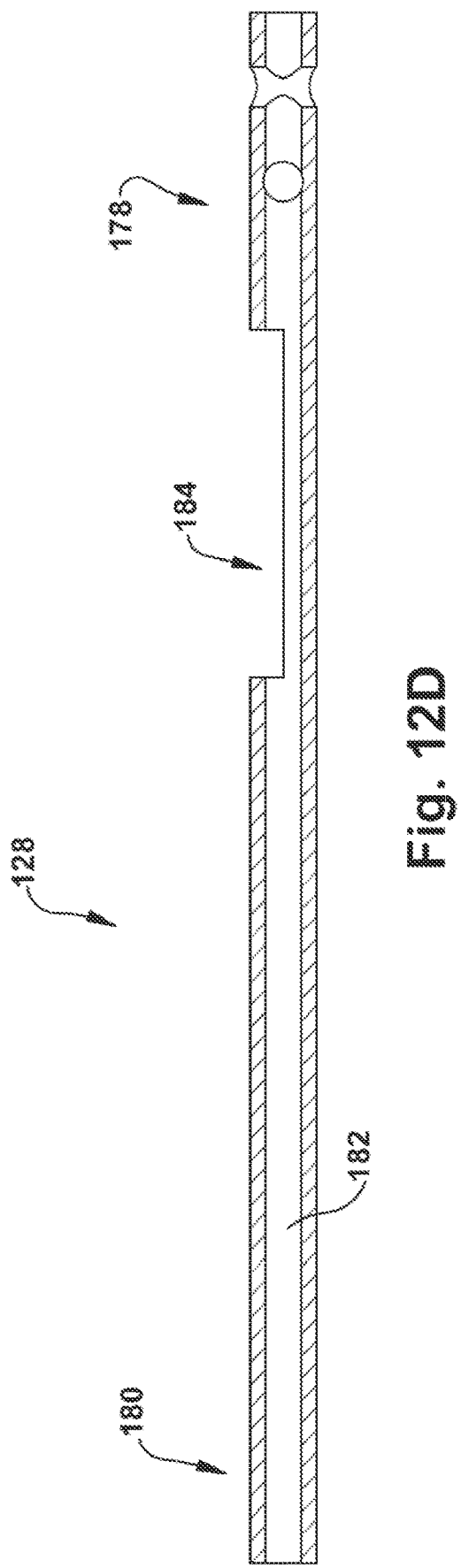

The elongated shaft 128 also includes an opening or slot 184. The slot 184 can be located about any portion of the elongated shaft 128. In one example, the slot 184 is located at or about the second end portion 180 of the elongated shaft 128. Although the slot 184 is shown in FIG. 12C as having a rectangular shape, it will be appreciated that the slot can have any desired shape (e.g., circular, square, ovoid, etc.). The slot 184 forms part of the central lumen 182, which extends through the elongated shaft 128 from the slot, through the first end portion 178, and through the hub portion 130. As described in more detail below, the slot 184 (and the central lumen 182) is adapted to receive an ejector lead 172 (FIG. 12G) therethrough.

Figure 12E:
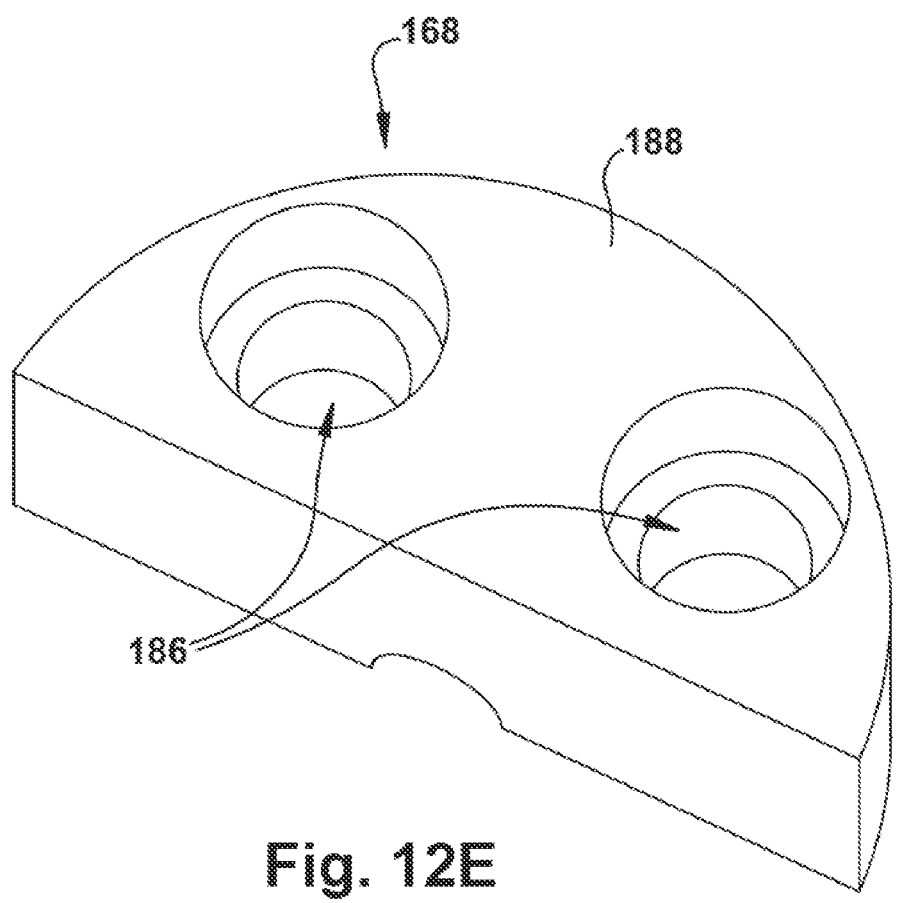
Figure 12F:
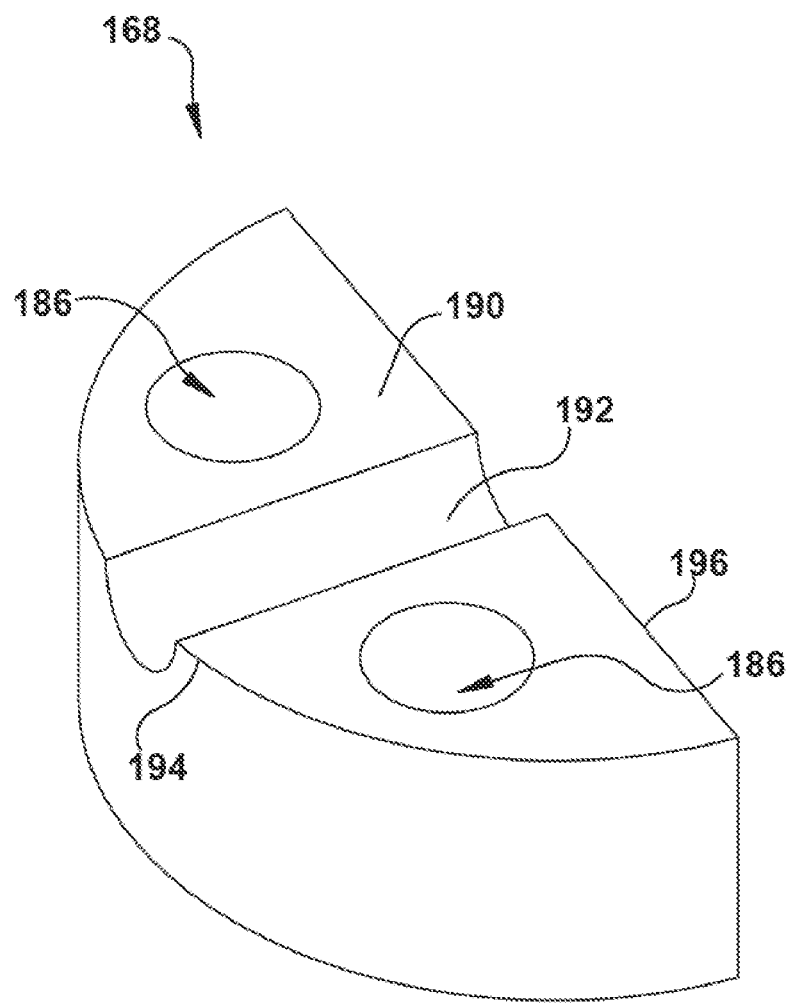

As shown in FIGS. 12E-F, the connector component 168 has a half-moon or semi-circular shape, and includes a plurality of channels 186 extending between first and second major surfaces 188 and 190 thereof. Each of the channels 186 is adapted to receive a fastener (e.g., a screw 174) so that the connector component 168 can be secured to the second component 140 of the handle 126. As shown in FIG. 12F, the second major surface 190 includes a groove 192, which is located between the channels 186 and extends between oppositely disposed first and second edges 194 and 196 of the connector component 168. The groove 192 is adapted to receive an L-shaped portion of the ejector lead 172. The connector component 168 can be formed from one or a combination of materials, such as a medical grade metal or metal alloy, medical grade plastics, polymers, or the like.

Figure 12G:
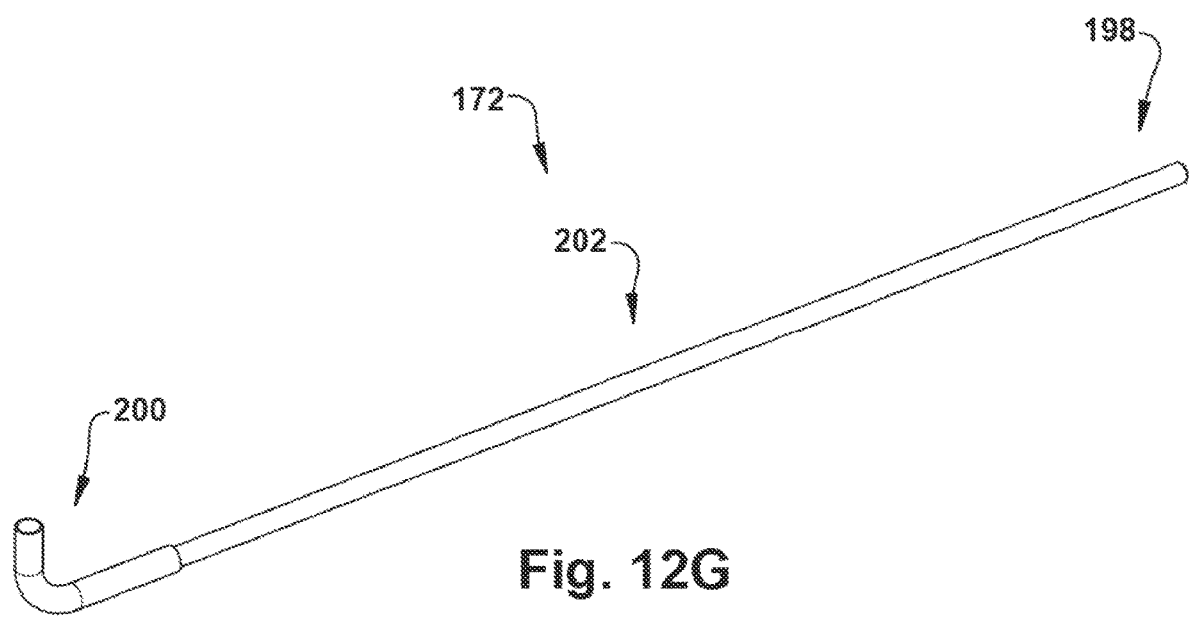

The ejector lead 172 is illustrated in FIG. 12G. The ejector lead 172 has a generally L-shaped configuration and includes a first end portion 198, a second end portion 200, and a main body portion 202 extending between the first and second end portions. Each of the first end portion 198 and the main body portion 202 have an elongated, wire-like shape adapted for insertion into the central lumen 182 of the elongated shaft 128. The second end portion 200 has an L- or elbow-shaped configuration and is adapted to extend through the slot 184 of the elongated shaft 128. As discussed in more detail below, the ejector lead 172 functions to displace the stimulation lead 22 of the neurostimulator 18 from the double barrel sheath 136 during operation of the delivery tool 124.

The hub portion 130 is located between the elongated shaft 128 and a trunk member 132. The hub portion 130 is sized and configured to releasably mate with a neurostimulator 18. The hub portion 130 comprises a port 204 configured to slidably receive a stimulator body 20 of the neurostimulator 18. The port 204 is defined by a lower surface 206, which is integrally formed with oppositely disposed side walls 208, as well as an upper portion 210 that includes a plurality of tangs 212. Although not shown, it will be appreciated that the upper portion 210 can include only one tang 212.

Figure 14:
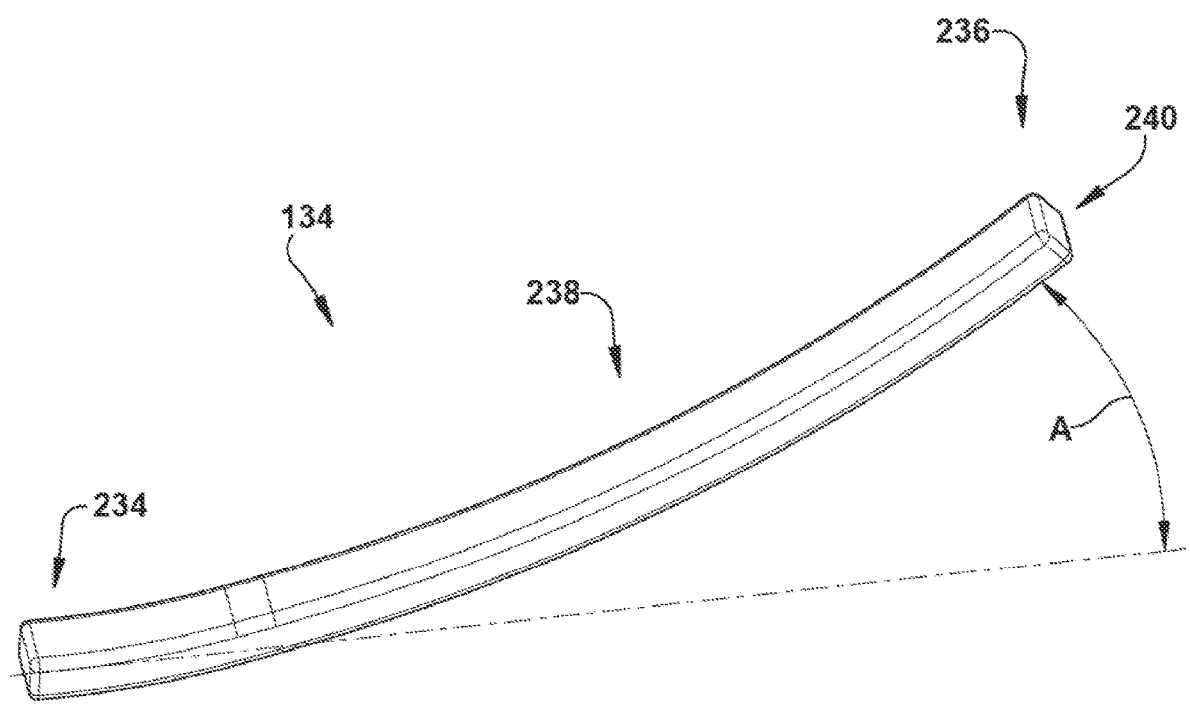
FIG. 14 is a perspective view of a spine member comprising the delivery tool in FIG. 10.

As mentioned above, a portion of the central lumen 182 extends through the hub portion 130. The hub portion 130 thus includes a second opening (not shown) that is in fluid communication with the central lumen 182. The lower surface 206 can be sized and dimensioned to allow the hub portion 130 to releasably mate with the neurostimulator 18. In one example, the lower surface 206 can have a length of about 0.5 cm to about 2 cm (e.g., about 1 cm). In another example, the lower surface 206 can have a width of about 0.5 cm to about 2 cm (e.g., about 1 cm). Each of the oppositely disposed side walls 208 can have any desired height, such as about 0.1 cm to about 0.5 cm (e.g., about 0.3 cm). As shown in FIG. 14A, each of the side walls 208 can have a contoured arcuate portion 214.

The tangs 212, in addition to the lower surface 206 and the side walls 208, are configured to provide a retention force when the stimulator body 20 is received in the port 204. Each of the tangs 212 includes an overhang portion 216 for contacting a portion of the stimulator body 20 (e.g., when the neurostimulator 18 is disposed in the port 204). Each of the overhang portions 216 permits the amount of a retention force between the stimulator body 20 and the hub portion 130 to be selectively adjusted. For example, bending of the integral fixation apparatus 26 of the neurostimulator 18 towards a surface 218 of the upper portion 210 creates opposing forces between the overhang portions 216 and a surface of the stimulator body 20. Increasing an adjustment angle of the integral fixation apparatus 26 towards the surface 218 results in an increased retention force. Removal of the retention force during retraction requires the integral fixation apparatus 26 to be pushed away from the surface 218.

The hub portion 130 can be made of a rigid or semi-rigid medical grade metal or metal alloy, such as stainless steel, medical grade plastics, polymers, or the like. The hub portion 130 is configured to hold or carry the neurostimulator body 20 during placement of the neurostimulator 18. Thus, one skilled in the art will appreciate that the amount of material used to form the hub portion 130 should be minimized to reduce the amount of tissue dissection needed to place the neurostimulator 18 in vivo, as well as to reduce the amount of drag that occurs during placement and removal of the delivery tool 124.

Figure 13A:
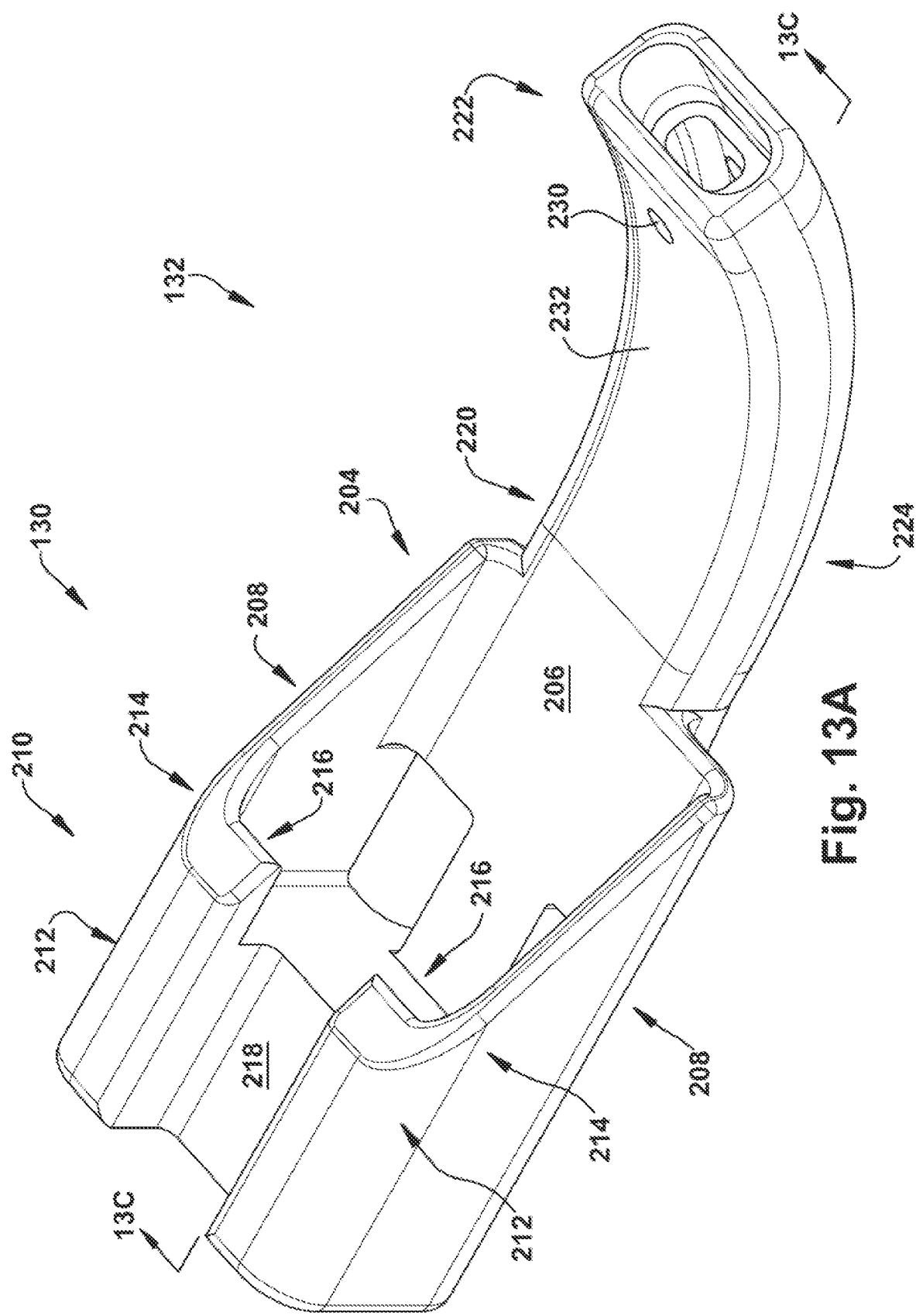
FIGS. 13A-B are perspective views of a hub portion comprising the delivery tool in FIG. 10.
Figure 13B:
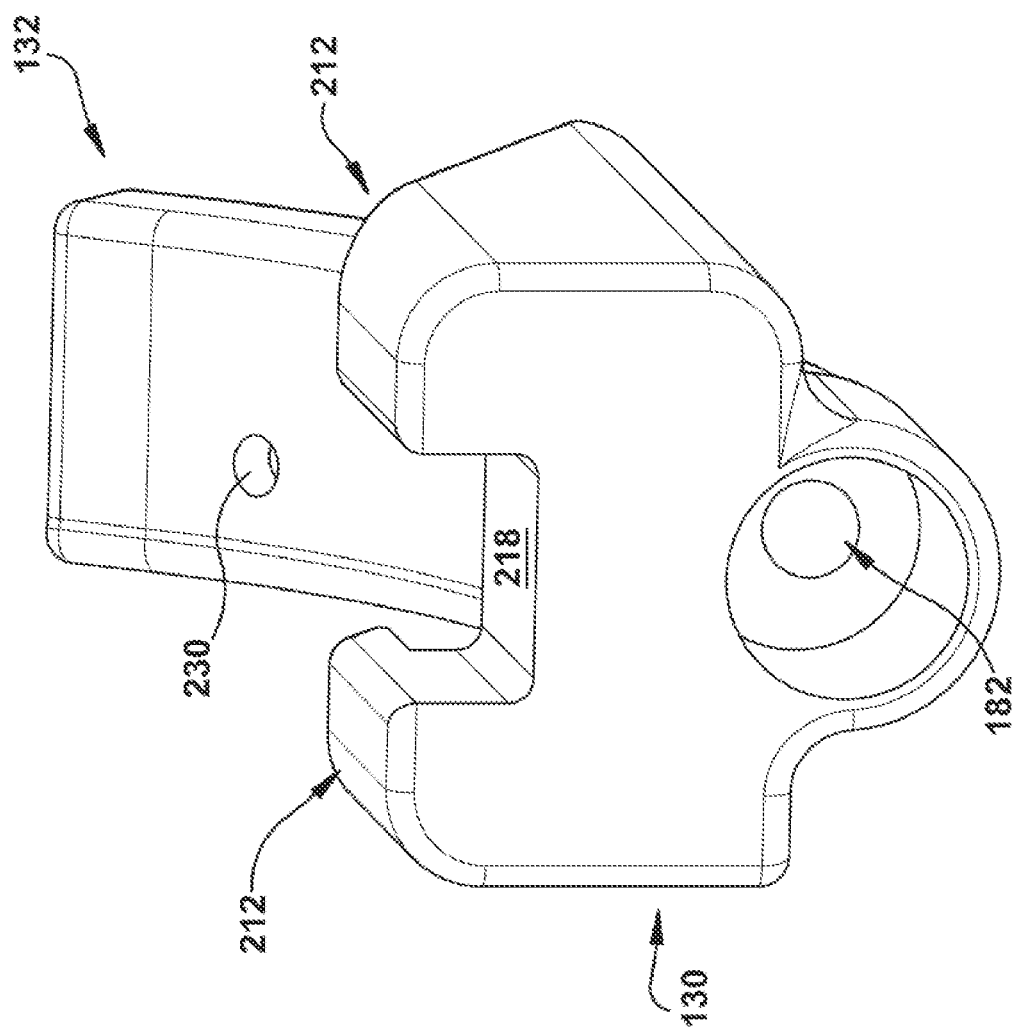
Figure 13C:
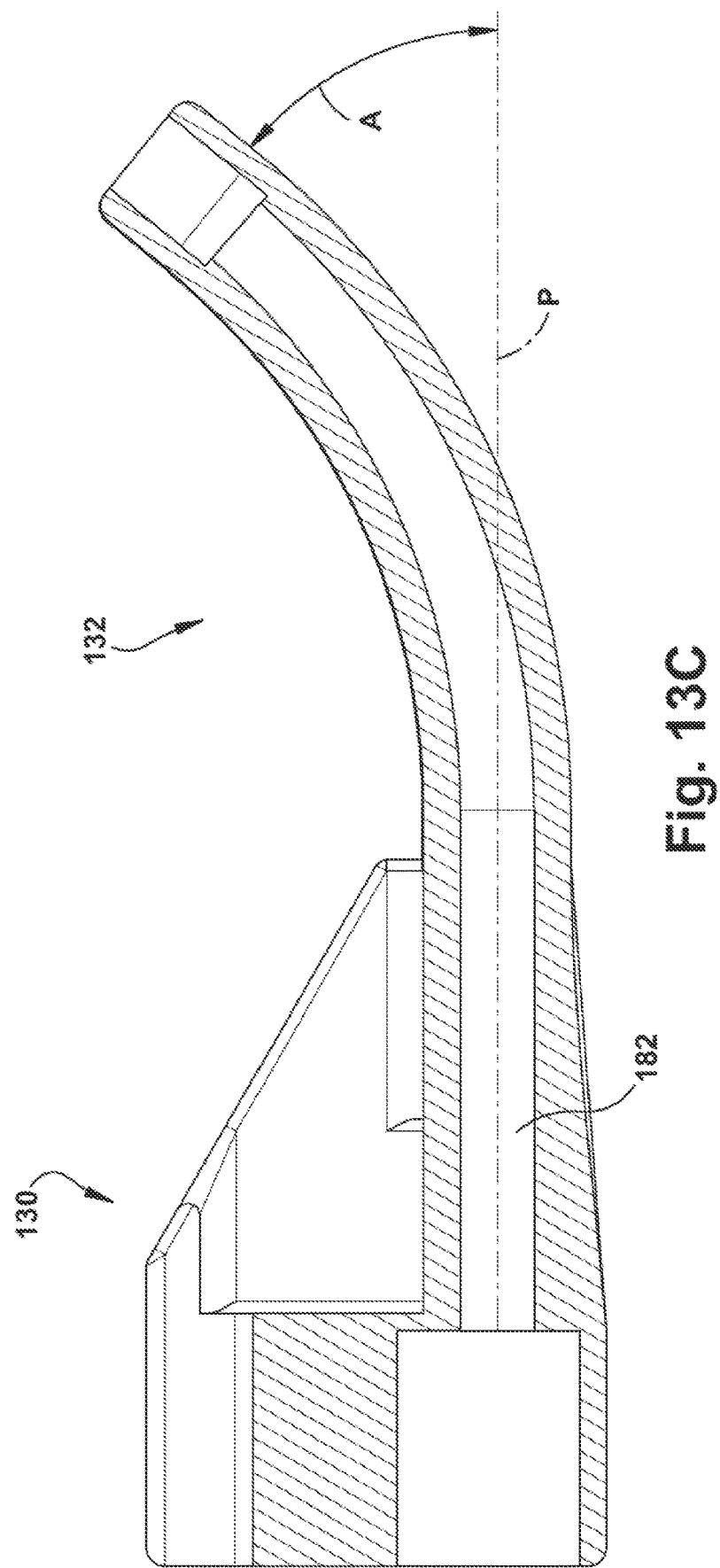
FIG. 13C is a cross-sectional view taken along Line 13C-13C in FIG. 13A.

In another aspect, the trunk member 132 (FIGS. 13A-C) is connected to (e.g., integrally formed with) and extends axially away from the hub portion 130. The trunk member 132 has an arcuate, elongated configuration and includes a proximal end portion 220, a distal end portion 222, and an intermediate portion 224 extending between the proximal and distal end portions. The proximal end portion 220 is connected (e.g., directly connected) to the hub portion 130. The trunk member 132 can have any desired length and width. In one example, the trunk member 132 can have a length of about 4 cm to about 6 cm (e.g., about 5 cm). In another example, the trunk member 132 can have a width of about 0.1 cm to about 0.8 cm (e.g., about 0.3 cm).

In some instances, the distal end portion 222 of the trunk member 132 can extend at an angle A (FIG. 14C) relative to a longitudinal plane P of the proximal end portion 220. In one example, the angle A can be about 10° to about 45°, depending upon the craniofacial anatomy of the subject.

First and second channels 226 and 228 can extend between the proximal and distal end portions 220 and 222 of the trunk member 132. The first channel 226 can be in fluid communication with the central lumen 182 of the hub portion 130 and the elongated shaft 128. In one example, the first channel 226 can have a circular cross-sectional shape. The second channel 228 can be sized and dimensioned to receive the spine member 134. In one example, the second channel 228 can have a rectangular cross-sectional profile. The trunk member 132 can include a channel 230 extending from an upper surface 232 thereof into communication with the second channel 228. The channel 230 is adapted to receive a fastener (e.g., a dowel) for securing the spine member 134 within the second channel 228.

In another aspect, the spine member 134 (FIG. 14) extends axially away from, and is securely connected to, the trunk member 132. The spine member 134 has an elongated configuration and includes a proximal end portion 234, a distal end portion 236, and an intermediate portion 238 extending between the proximal and distal end portions. The proximal end portion 234 is adapted for connection to the trunk member 132 via insertion into the second channel 228. The spine member 134 can be secured in the second channel 228 by a fastener (e.g., a dowel) inserted through the channel 230 of the trunk member 132.

The spine member 134 can have any desired length and width. In one example, the spine member 134 can have a length of about 4 cm to about 6 cm (e.g., about 5 cm). In another example, the spine member 134 can have a width of about 0.1 cm to about 0.8 cm (e.g., about 0.3 cm). The spine member 134 can have a uniform width or, alternatively, the width of the spine member can taper from a first width at the proximal end portion 234 that is greater than a second width at the distal end portion 236. In some instances, a distal tip 240 of the spine member 134 can include a tapered arcuate end. In other instances, the distal tip 240 can be bulbous or mushroom-shaped. In some instances, the spine member 134 can have a square-shaped cross-sectional profile; however, it will be appreciated that other cross-sectional profiles are possible (e.g., semi-circular, circular, rectangular, etc.).

In some instances, the distal end portion 236 of the spine member 134 can extend at an angle A relative to a longitudinal plane P of the proximal end portion 234. In one example, the angle A can be about 10° to about 45°, depending upon the craniofacial anatomy of the subject.

The spine member 134 can have a rigid, semi-rigid, or flexible configuration. The spine member 134 can be made from one or combination of rigid, semi-rigid, or flexible materials, such as metals, metal alloys, and polymers or plastics. In some instances, all or only a portion of the spine member 134 can be malleable. For example, only the distal end portion 236 of the spine member 134 can be malleable. In another example, the spine member 134 can be made of a malleable metal that supports the double barrel sheath 136 and the integral stimulation lead 22 from buckling when longitudinal or lateral forces are encountered. The malleability allows a physician to conform the shape of the neurostimulator 18 (e.g., the integral stimulation lead 22) to correspond to a patient's anatomy and thereby aid with implantation. Malleability in some cases is not required; thus, a spine member 134 made from a non-malleable material, such as plastic can also serve the intended function.

Figure 15A:
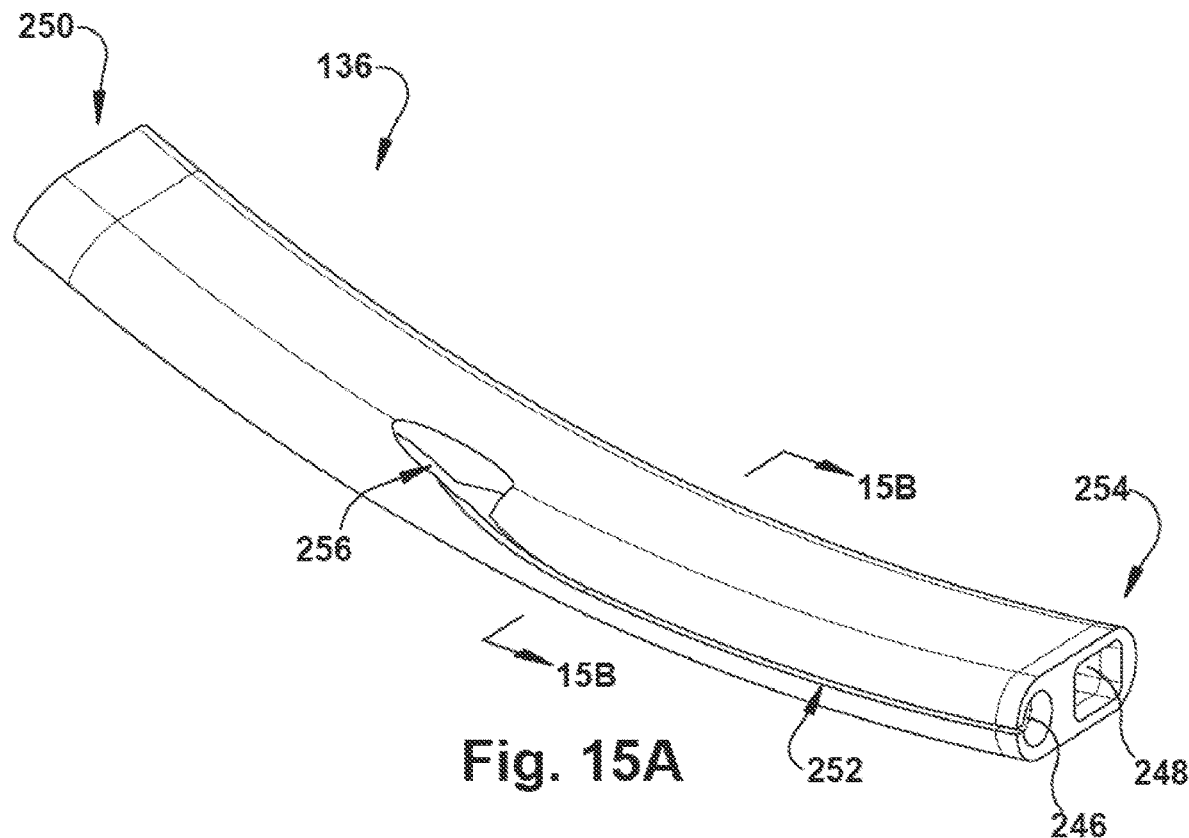
FIG. 15A is a perspective view of a double barrel sheath comprising the delivery tool in FIG. 10.
Figure 15B:
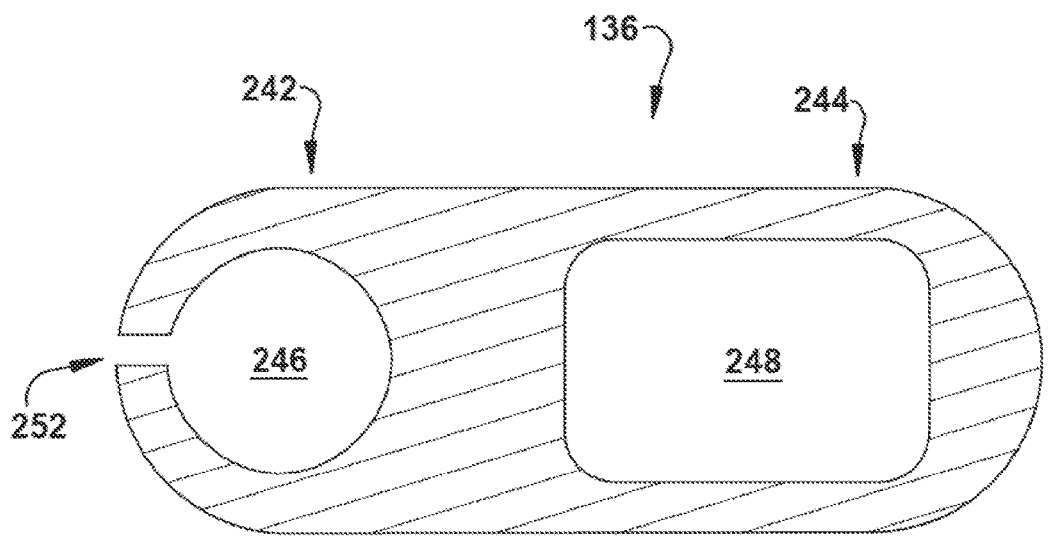
FIG. 15B is a cross-sectional view taken along Line 15B-15B in FIG. 15A.
Figure 15C:
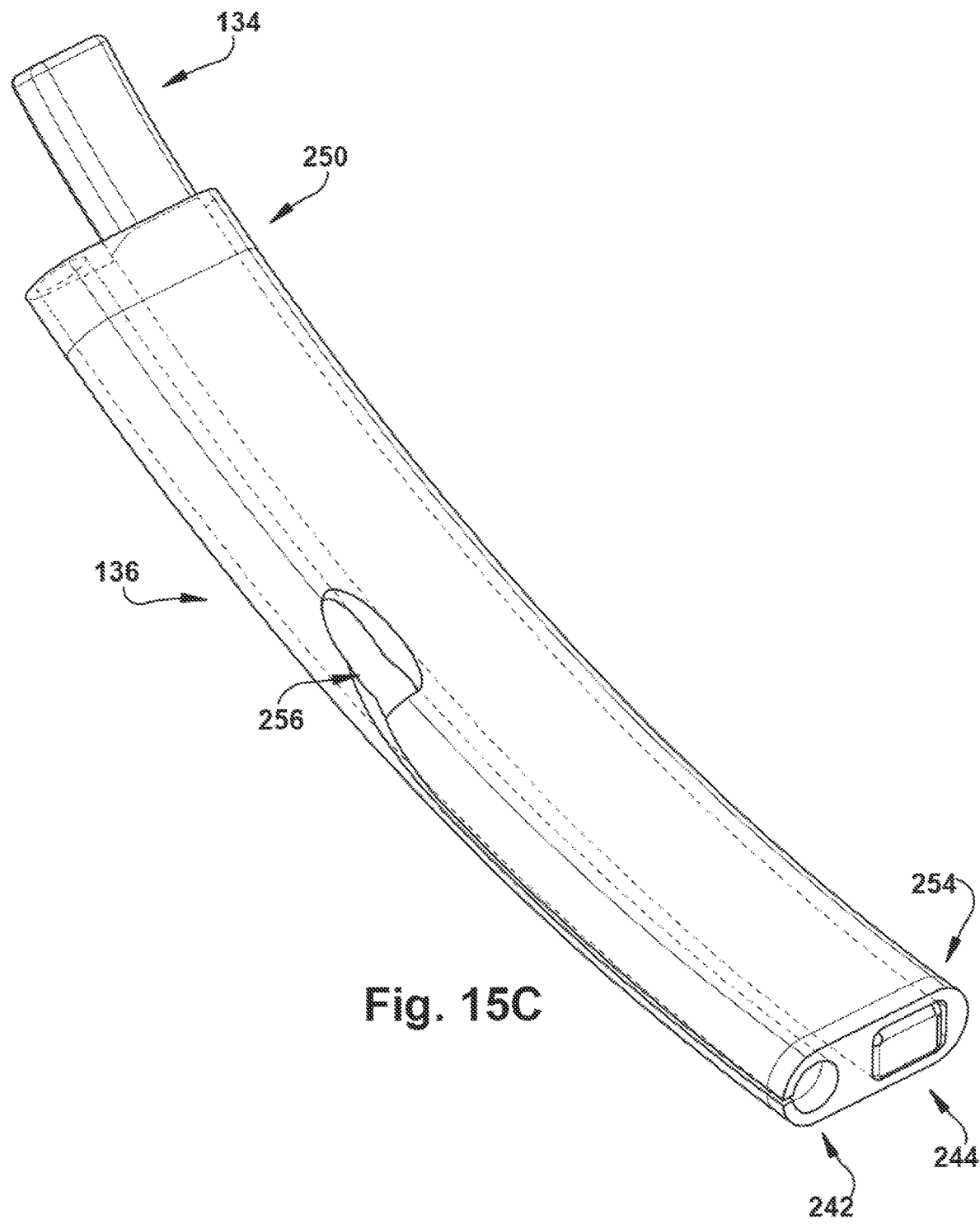
FIG. 15C is a perspective view of the spine member in FIG. 14 mated with the double barrel sheath (FIGS. 15A-C)

In another aspect, the delivery tool 124 includes a double barrel sheath 136 (FIGS. 15A-C) that is connected to the spine member 134. The double barrel sheath 136 comprises a first barrel 242 and a second barrel 244. A first lumen 246 and a second lumen 248 extend through the first and second barrels 242 and 244, respectively. As shown in FIG. 15B, the second lumen 248 can have a rectangular cross-sectional profile and be shaped and dimensioned to receive all or only a portion of the spine member 134. The first lumen 246 can have a circular cross-sectional profile and be shaped and dimensioned to partially receive the integral stimulation lead 22 of the neurostimulator 18. A first end 250 of the double barrel sheath 136 is securely connected to the trunk member 132 so that the central lumen 182 is in fluid communication with the first lumen 246. The double barrel sheath 136 can be securely connected to the trunk member 132 by any one or combination of attachment mechanisms, such as adhesives, pins, staples, etc.

In some instances, the double barrel sheath 136 can be made of a semi-flexible material (or materials). In one example, the double barrel sheath 136 can be formed from a plastic or polymer, such as polytetrafluoroethylene. In other instances, the double barrel sheath 136 can be formed from a flexible material having a thickness of about 0.04 inches to about 0.001 inches.

In some instances, the first barrel 242 of the sheath 136 has a splittable configuration to allow for removal or deployment of the integral stimulation lead 22 of the neurostimulator 18 from the sheath with minimal load on the integral stimulation lead. A partial section of the first barrel 242 can include a seam 252 adapted to permit egress of the stimulation lead 22 from the first lumen 246 during deployment of the neurostimulator 18. The seam 252 can extend from a second end 254 of the sheath 136 to an opening 256, which is located at or about the midpoint of the first barrel 242. In some instances, the distance between the second end 254 and the opening 256 can be equal to, or about equal to, the length of the stimulation lead 22. The seam 252 allows for removal or deployment of the integral stimulation lead 22 of the neurostimulator 18 from the sheath 136 with minimal load on the integral stimulation lead. Undesirable loading on the integral stimulation lead 22 can cause migration of the lead away from the desired implant location during withdrawal of the delivery tool 124. Advantageously, only the seam 252 of the sheath 136 is parted during deployment of the neurostimulator 18, which reduces the load on the integral stimulation lead 22.

Figure 16:
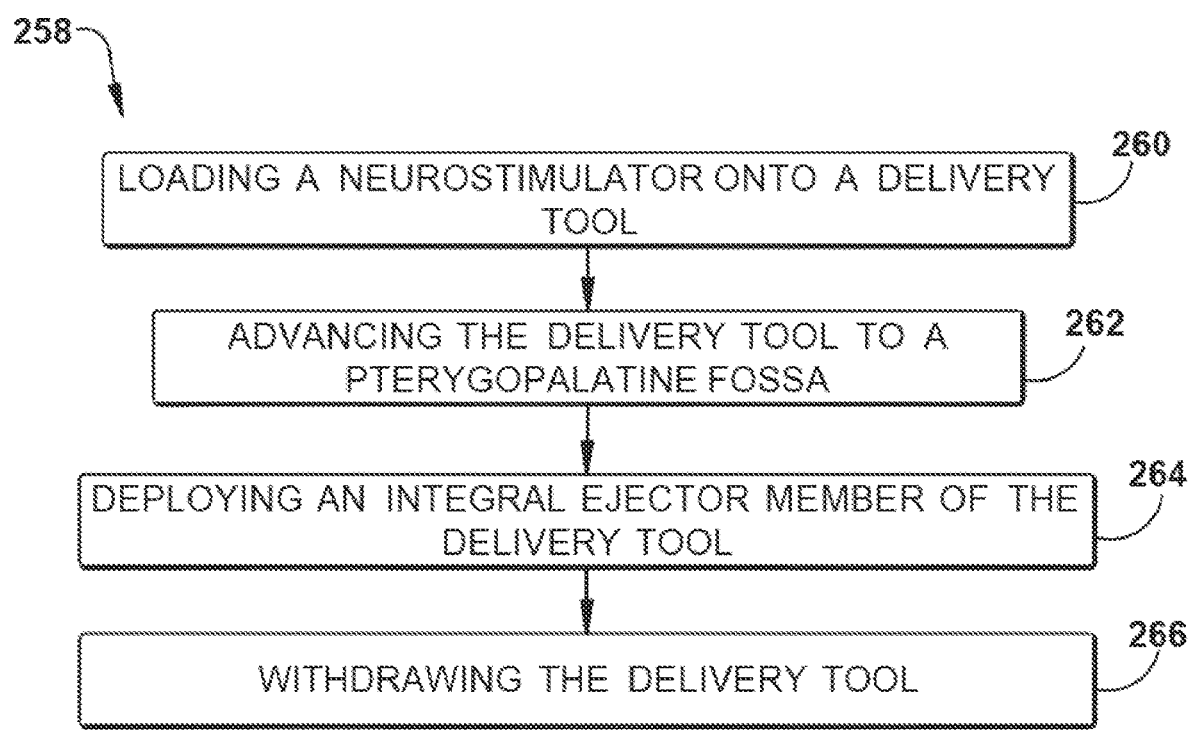
FIG. 16 is a process flow diagram illustrating a method for deploying a neurostimulator in close proximity to a SPG of a subject according to another aspect of the present disclosure.

Another aspect of the present disclosure is illustrated in FIG. 16 and includes a navigation-assisted method 258 for deploying a neurostimulator 18 in close proximity to a SPG 10 of a subject. The method 258 can generally include the steps of: loading a neurostimulator 18 onto a delivery tool 124 (Step 260); advancing the delivery tool to a PPF 14 (Step 262); deploying an integral lead ejector 172 of the delivery tool (Step 264); and withdrawing the delivery tool from the subject (Step 266). In one example of the method 258, the delivery tool 124 is configured as shown in FIG. 10 and described above, and the neurostimulator 18 is configured as shown in FIG. 2 and described in the '641 patent. Steps 262-266 of the method 258 can be performed using a commercially available navigation system, such as the KICK or CURVE systems (BRAINLAB, Westchester, IL), the FUSION ENT navigation system (Medtronic, Minneapolis, MN), or the NAV3 Navigation Platform (Stryker, Kalamazoo, MI).

Figure 17A:
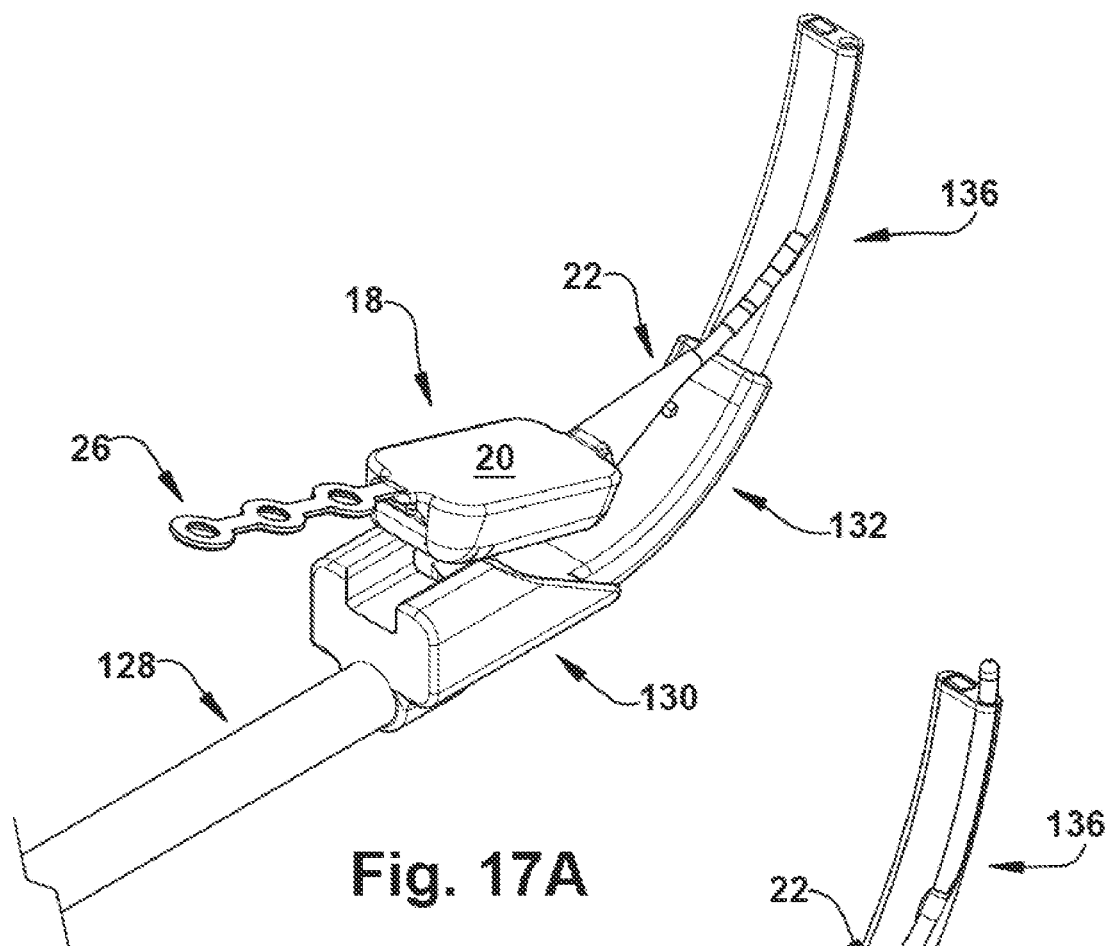
FIGS. 17A-D are a series of schematic illustrations showing loading and deployment of a neurostimulator from the delivery tool in FIG. 10.
Figure 17B:
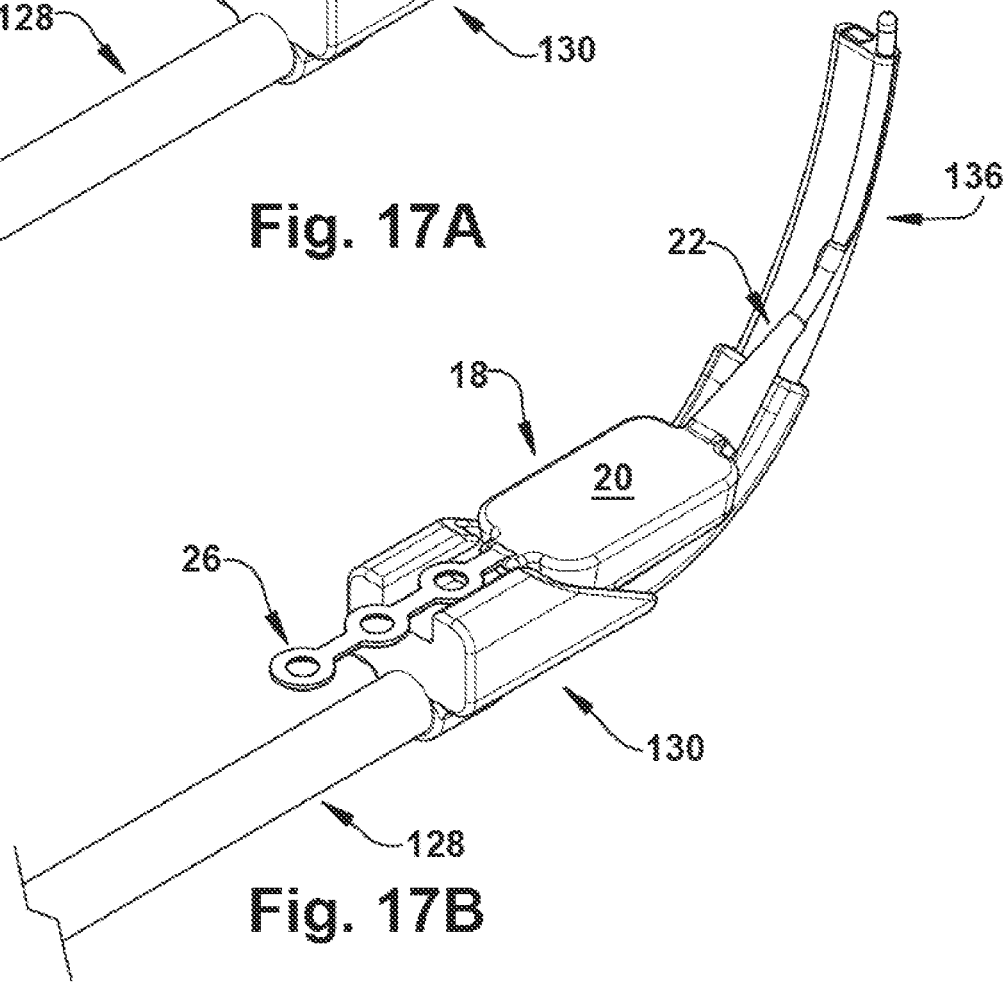
Figure 17C:
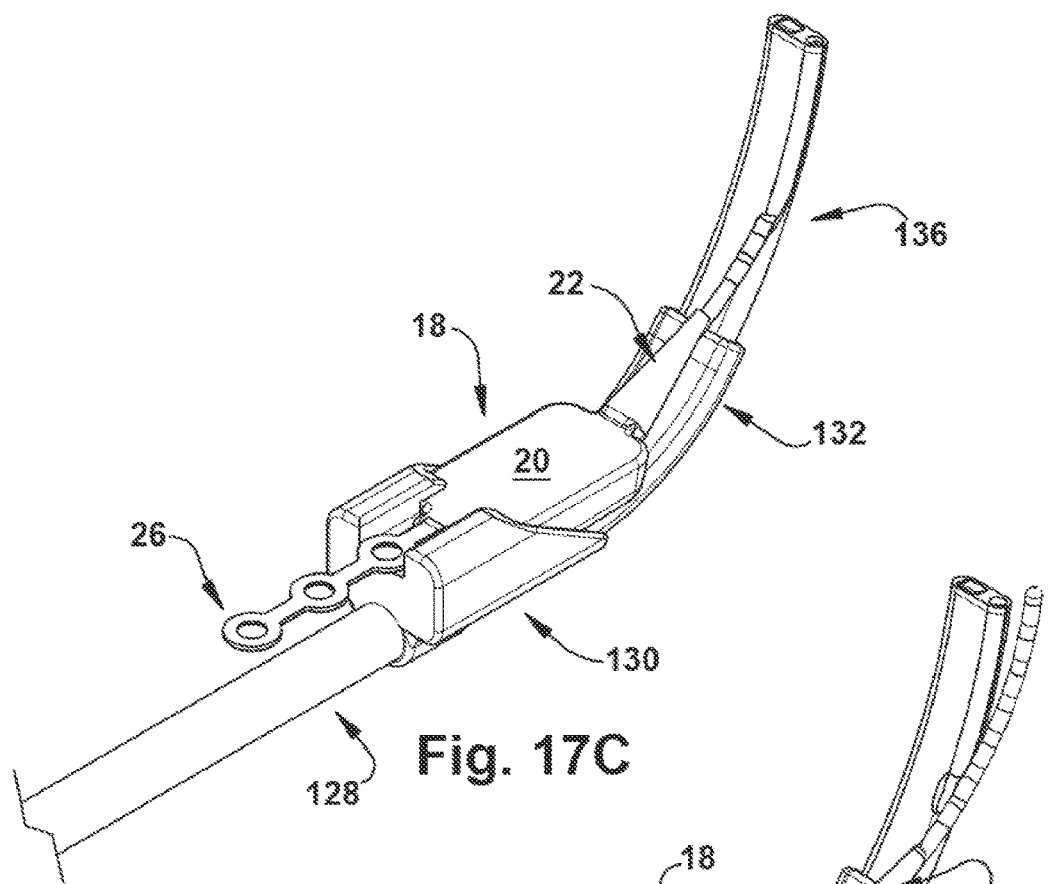
Figure 17D:
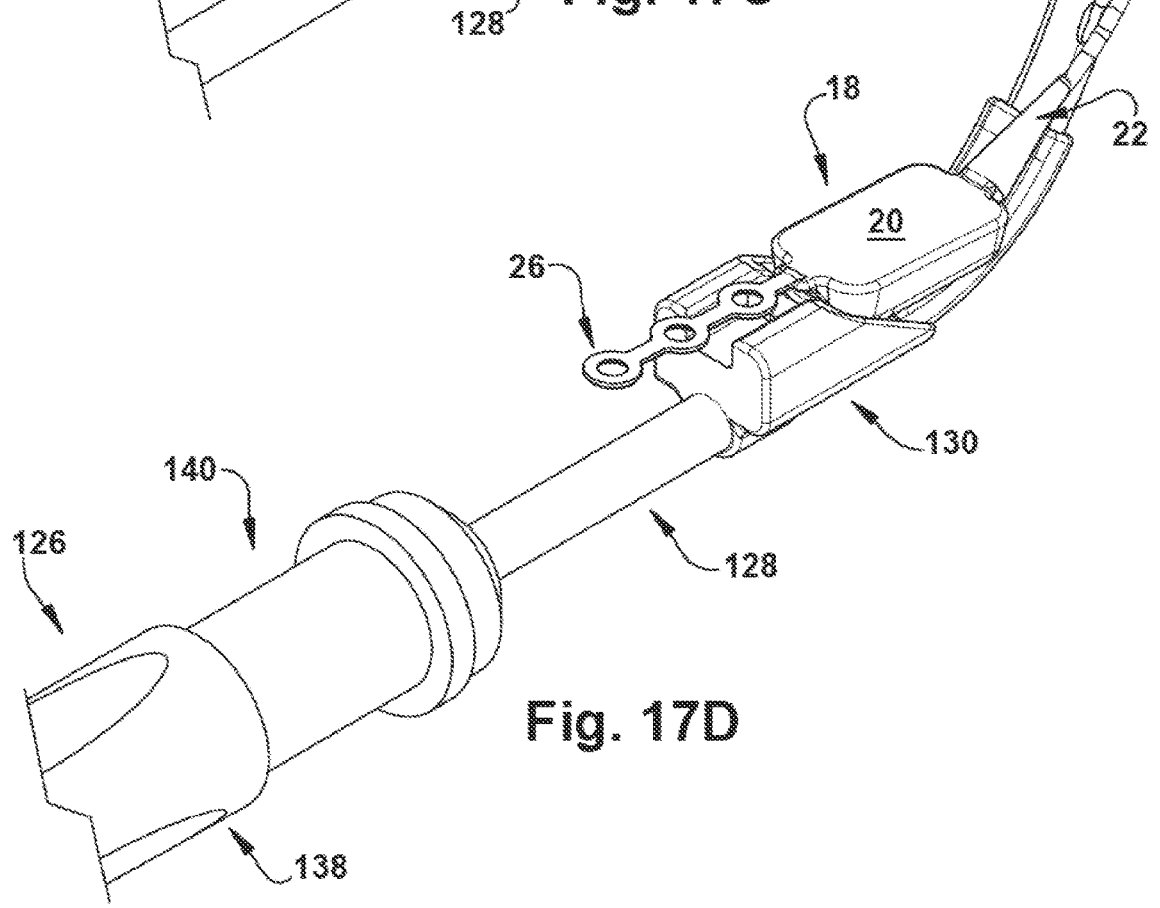

Either prior to, contemporaneous with, or following Step 260, a delivery path can be surgically formed in the subject as disclosed in the '480 application. Loading of the neurostimulator 18 onto the delivery tool 124 is illustrated in FIGS. 17A-C. To do so, the neurostimulator 18 is first brought into close proximity with the hub portion 130 of the delivery tool 124. The neurostimulator 18 is then angled slight downward toward the double barrel sheath 136 of the delivery tool 124 until a distal portion of the integral stimulator lead 22 is introduced or inserted into the opening 256 of the sheath (FIG. 17A). Next, the neurostimulator 18 is progressively advanced in a distal direction until a portion of the neurostimulator body 20 is in flush contact with the lower surface 206 of the hub portion 130 (FIG. 17B). As shown in FIG. 17C, the neurostimulator 18 is then advanced towards the handle 126 of the delivery tool 124 until the neurostimulator body 20 snugly engages the tangs 212 and the integral fixation apparatus 26 engages the surface 218 of the hub portion 130, thereby providing a retention force to keep the neurostimulator securely mated with the delivery tool during implantation.

To form the delivery path, a gingival-buccal insertion site in a similar or identical manner as disclosed in the '258 application. In one example, a #10 scalpel blade (not shown) can be used to make an incision in a horizontal manner between the second and third molars (not shown). Next, a first surgical tool (not shown) similar or identical to the one disclosed in the '480 application is inserted into the incision and subperiosteally. In some instances, the anatomy of the subject's skull, including the location and size of the PPF 14 can be determined prior to insertion of the first surgical tool. After inserting the first surgical tool into the incision, the first surgical tool is urged in a posterior direction so that a first major surface of the surgical tool's distal portion traverses under the zygomatic bone 28 along the maxillary tuberosity 120. The first surgical tool is then advanced further until a distal dissecting tip thereof engages the junction formed by the posterior maxillary buttress (not shown) and the pterygoid plate 122, just inferior and lateral to the PPF 14. Advancement of the first surgical tool may naturally stop when the distal dissecting tip is correctly positioned at the junction formed by the posterior maxillary buttress and the pterygoid plate 122. The first surgical tool is then withdrawn, thereby creating a surgical access cavity (not shown).

After forming the delivery path, the delivery tool 124 (with the neurostimulator 18 loaded thereon) can be advanced through the delivery path until the stimulation lead 22 of the neurostimulator is adjacent the PPF 14 (Step 262). At Step 266, the handle 126 of the delivery tool 124 can be manipulated by, for example, sliding the second component 140 axially away from the first component 138. The second component 140 can be sufficiently advanced (relative to the first component 138) to cause the lead ejector 172 of the delivery tool 124 to advance through the central lumen 182, which causes the stimulation lead 22 to emerge from the seam 252 of the double barrel sheath 136 so that the stimulation lead is in close proximity to the SPG 10.

At Step 266, the delivery tool 124 can be withdrawn so that the neurostimulator 18 remains implanted in the subject as disclosed in the '641 patent. Following completion of the surgery, and with the neurostimulator 18 securely implanted within the subject, an electrical current from the neurostimulator can be applied to the SPG 10 to treat a medical condition (e.g., headache).

From the above description of the invention, those skilled in the art will perceive improvements, changes and modifications. Such improvements, changes and modifications within the skill of the art are intended to be covered by the appended claims. All patents, patent applications, and publication cited herein are incorporated by reference in their entirety.

The following is claimed:

1. A method for deploying an electrode in the skull of a subject, the electrode including a body connected to an integral electrode lead, the method comprising the steps of:
   (a) loading the electrode onto a delivery tool;
   (b) advancing the delivery tool so that the electrode lead of the electrode is inserted through the skull of the patient;
   (c) ejecting the electrode lead from the delivery tool so that the electrode lead is positioned in the skull of the subject, wherein said ejecting the electrode comprises deploying an integral lead ejector from the delivery tool; and
   (d) withdrawing the delivery tool so that the electrode lead remains implanted in the subject.

2. The method set forth in claim 1, wherein steps (b)-(d) are performed using a navigation system.

3. The method set forth in claim 2, wherein steps (c) and (d) are performed simultaneously.

4. The method set forth in claim 1, wherein the electrode is a neurostimulator.

5. The method set forth in claim 1, further comprising delivering an electrical signal through the electrode after said withdrawing the delivery tool.

6. The method set forth in claim 1, wherein the body of the electrode remains outside the skull after said withdrawing the delivery tool.

7. The method set forth in claim 1, wherein said loading the electrode comprises releasably coupling the delivery tool to the body of the electrode.

\* \* \* \* \*